United States Patent
Pompejus et al.

(10) Patent No.: US 6,878,536 B2
(45) Date of Patent: Apr. 12, 2005

(54) PHOSPHORIBOXYL-PYROPHOSPHATE SYNTHETASE POLYPEPTIDE

(75) Inventors: Markus Pompejus, Waldsee (DE); Harald Seulberger, Neuhofen (DE); Hans Wolfgang Höffken, Ludwigshafen (DE); Jose Luis Revuelta Doval, Salamanca (ES); Alberto Jimenez, Salamanca (ES); Maria Angeles Santos Garcia, Salamanco (ES)

(73) Assignee: BASF, Ludwigshafen (DE)

( * ) Notice: Subject to any disclaimer, the term of this patent is extended or adjusted under 35 U.S.C. 154(b) by 302 days.

(21) Appl. No.: 10/076,157

(22) Filed: Feb. 15, 2002

(65) Prior Publication Data

US 2003/0027309 A1 Feb. 6, 2003

Related U.S. Application Data

(62) Division of application No. 09/212,247, filed on Dec. 16, 1998, now Pat. No. 6,391,603.

(30) Foreign Application Priority Data

Dec. 23, 1997 (DE) .......................................... 197 57 755

(51) Int. Cl.⁷ ................................................. C12N 9/12
(52) U.S. Cl. ....................................................... 435/194
(58) Field of Search ......................................... 435/194

(56) References Cited

U.S. PATENT DOCUMENTS 5,821,090 A  10/1998  Doval et al. ................... 435/88

FOREIGN PATENT DOCUMENTS

EP  405370  1/1991

OTHER PUBLICATIONS

Branden et al. "Introduction to Protein Structure", Garland Publishing Inc., New York, 1991.*
Witkowski et al. (1999) Biochemistry 38:11643–11650.*
Database GenBank Accession No. P38620, Oct. 1994.*
Voet et al., *Biochemistry*, 1994, p/743–771.
Zalkin et al., *Progress in Nucleic Acid Research & Molecular Biol*, vol. 42, 1992, p. 259–287.
Christopherson et al., *Med. Res. Reviews*, vol. 10, No. 4, p. 505–548, 1990.
Smith, *Current Opinion in Structural Biology*, vol. 5, No. 1, p. 752–757, 1995.
Simmonds, *Biochem. Soc. Transact.*, vol. 23, p. 877–902, 1995.

* cited by examiner

*Primary Examiner*—David J. Steadman
(74) *Attorney, Agent, or Firm*—Novak Druce & Quigg LLP

(57) ABSTRACT

Genes of purine biosynthesis from *Ashbya gossypii* are used in microbial riboflavin synthesis.

1 Claim, 2 Drawing Sheets

Inhibition of wild-type and mutagenized KPRS by ADP

PHOSPHORIBOXYL-PYROPHOSPHATE SYNTHETASE POLYPEPTIDE

This application is a divisional of U.S. non-provisional application No. 09/212,247, filed Dec. 16, 1998, now U.S. Pat. No. 6,391,603.

The present invention relates to genes of purine biosynthesis from *Ashbya gossypii* and to the use thereof in riboflavin synthesis.

Vitamin B2, also called riboflavin, is essential for humans and animals. Vitamin B2 deficiency is associated with inflammations of the mucous membranes of the mouth and throat, itching and inflammations in the skin folds and similar cutaneous lesions, conjunctival inflammations, reduced visual accuracy and clouding of the cornea. Babies and children may experience cessation of growth and loss of weight. Vitamin B2 therefore has economic importance, especially as vitamin supplement in cases of vitamin deficiency and as supplement to animal feed. It is also employed for coloring foodstuffs, for example in mayonnaise, icecream, blancmange etc.

Vitamin B2 is prepared either chemically or microbially (see, for example, Kurth et al. (1996) riboflavin, in: Ullmann's Encyclopedia of industrial chemistry, VCH Weinheim). In the chemical preparation process, riboflavin is, as a rule, obtained as pure final product in multistage processes, it being necessary to employ relatively costly starting materials such as, for example, D-ribose. An alternative to the chemical synthesis of riboflavin is the preparation of this substance by microorganisms. The starting materials used in this case are renewable raw materials such as sugars or vegetable oils. The preparation of riboflavin by fermentation of fungi such as *Eremothecium ashbyii* or *Ashbya gossypii* is known (The Merck Index, Windholz et al., eds. Merck & Co., page 1183, 1983), but yeasts such as, for example, *Candida, Pichia* and *Saccharomyces*, or bacteria such as, for example, *Bacillus, clostridia* or *corynebacteria*, have also been described as riboflavin producers.

EP 405370 describes riboflavin-overproducing bacterial strains obtained by transformation of the riboflavin biosynthesis genes from *Bacillus subtilis*. These genes described therein, and other genes involved in vitamin B2 biosynthesis from prokaryotes are unsuitable for a recombinant riboflavin preparation process using eukaryotes such as, for example, *Saccharomyces cerevisiae* or *Ashbya gossypii*.

DE 44 20 785 describes six riboflavin biosynthesis genes from *Ashbya gossypii*, and microorganisms transformed with these genes, and the use of such microorganisms for riboflavin synthesis.

It is possible with these processes to generate producer strains for microbial riboflavin synthesis. However, these producer strains often have metabolic limitations which cannot be eliminated by the inserted biosynthesis genes or are sometimes induced thereby. Such producer strains are sometimes unable to provide sufficient substrate for saturating some steps in the biosynthesis, so that the biosynthetic capacity of some segments of metabolism cannot be fully exploited.

It is therefore desirable to enhance further sections of metabolic pathways, thereby to eliminate metabolic bottlenecks and thus further optimize the microorganism employed for the microbial riboflavin synthesis (producer strains) in respect of their ability for riboflavin synthesis. It is desirable to identify the enhancing sections of the complex metabolism and to enhance these in a suitable way.

The present invention relates to novel proteins of purine biosynthesis, the genes therefor and the use thereof for microbial riboflavin synthesis.

Purine metabolism (for a review, see, for example, Voet, D. and Voet, J. G., 1994, Biochemie, VCH Weinheim, pages 743–771; Zalkin, H. and Dixon, J. E., 1992, De novo purine nucleotide biosynthesis, in: Progress in nucleic acid research and molecular biology, Vol. 42, pages 259–287, Academic Press) is a part of the metabolism which is essential for all life forms. Faulty purine metabolism may in humans lead to serious diseases (e.g. gout). Purine metabolism is moreover an important target for treating oncoses and viral infections. Numerous publications have appeared describing substances which intervene in purine metabolism for these indications (as review, for example Christopherson, R. I. and Lyons, S. D., 1990, Potent inhibitors of de novo pyrimidine and purine biosynthesis as chemotherapeutic agents, Med. Res. Reviews 10, pages 505–548).

Investigations on the enzymes involved in purine metabolism (Smith, J. L., Enzymes in nucleotide synthesis, 1995, Curr. Opinion Struct. Biol. 5, 752–757) aim to develop novel immunosuppressives, antiparasitic or antiproliferative medicines (Biochem. Soc. Transact. 23, pages 877–902, 1995).

These medicines are normally not naturally occurring purines, pyrimidines or compounds derived therefrom.

The present invention relates to a protein having the polypeptide sequence depicted in SEQ ID NO:2 or a polypeptide sequence obtainable from SEQ ID NO:2 by substitution, insertion or deletion of up to 15% of the amino acids, and having the enzymatic activity of a phosphoribosyl-pyrophosphate synthetase.

The sequence depicted in SEQ ID NO:2 is the gene product of the KPR1 gene (SEQ ID NO:1) obtained from *Ashbya gossypii*.

The invention further relates to a protein having the polypeptide sequence depicted in SEQ ID NO:5 or a polypeptide sequence obtainable from SEQ ID NO:5 by substitution, insertion or deletion of up to 10% of the amino acids, and having the enzymatic activity of a glutamine-phosphoribosyl-pyrophosphate amidotransferase.

The sequence depicted in SEQ ID NO:5 is the gene product of the ADE4 gene (SEQ ID NO:3) obtained from *Ashbya gossypii*.

The invention further relates to a protein having the polypeptide sequence depicted in SEQ ID NO:8 or a polypeptide sequence obtainable from SEQ ID NO:8 by substitution, insertion or deletion of up to 20% of the amino acids, and having the enzymatic activity of an IMP dehydrogenase.

The sequence depicted in SEQ ID NO:8 and 9 is the gene product of the GUA1 gene (SEQ ID NO:7) obtained from *Ashbya gossypii*.

The invention further relates to a protein having the polypeptide sequence depicted in SEQ ID NO:11 or a polypeptide sequence obtainable from SEQ ID NO:11 by substitution, insertion or deletion of up to 10% of the amino acids, and having the enzymatic activity of a GMP synthetase.

The sequence depicted in SEQ ID NO:11 is the gene product of the GUA2 gene (SEQ ID NO:10) obtained from *Ashbya gossypii*.

The invention further relates to a protein having the polypeptide sequence depicted in SEQ ID NO:13 or a polypeptide sequence obtainable from SEQ ID NO:13 by substitution, insertion or deletion of up to 10% of the amino acids, and having the enzymatic activity of a phosphoribosyl-pyrophosphate synthetase.

The sequence depicted in SEQ ID NO:13 is the gene product of the KPR2 gene (SEQ ID NO:12) obtained from *Ashbya gossypii*.

These gene products mentioned can be modified by conventional methods of gene technology, such as site-directed mutagenesis, so that particular amino acids are replaced, additionally inserted or deleted. Amino acid residues are normally (but not exclusively) replaced by those of similar volume, charge or hydrophilicity/hydrophobicity in order not to lose the enzymatic properties of the gene products. In particular, modifications of the amino acid sequence in the active center frequently results in a drastic alteration in the enzymatic activities. However, modifications of the amino acid sequence and other, less essential sites are often tolerated.

It is possible with the novel proteins
1. for up to 15, preferably up to 10 and particularly preferably up to 5%, of the amino acids to be modified, by comparison with sequences depicted in the sequence listing, in the case of the gene product of the AgKPR1 gene;
2. for up to 10 and particularly preferably up to 5% of the amino acids to be modified, by comparison with the sequences depicted in the sequence listing, in the case of the gene product of the AgADE4 gene;
3. for up to 20, preferably up to 15, particularly preferably up to 10 and especially preferably up to 5%, of the amino acids to be modified, by comparison with the sequences depicted in the sequence listing, in the case of the gene product of the AgGUA1 gene;
4. for up to 10 and particularly preferably up to 5% of the amino acids to be modified, by comparison with the sequences depicted in the sequence listing, in the case of the gene product of the AgGUA2 gene;
5. for up to 10%, preferably up to 7% and particularly preferably up to 5%, of the amino acids to be modified, by comparison with the sequences depicted in the sequence listing, in the case of the gene product of the AgKPR2 gene.

Preferred proteins are those which, while they still have the relevant enzymatic activity, have altered regulation. Many of these enzymes are subject to a strong control of the activity by intermediates and final products (feedback inhibition). This leads to the activity of the enzymes being restricted as soon as sufficient final product is present.

However, in the case of producer strains, this economic control in the physiological state often results in it being impossible to increase the productivity beyond a certain limit. Elimination of such feedback inhibition results in the enzymes retaining their activity, irrespective of the final product concentration, and thus metabolic bottlenecks are bypassed. This in the end leads to a marked increase in riboflavin biosynthesis.

Preferred novel proteins are those no longer inhibited by secondary products of metabolic pathways (derived from products of the enzymes). Particularly preferred novel proteins are those no longer inhibited by intermediates of purine biosynthesis, in particular by purine bases, purine nucleosides, purine nucleotide 5'-monophosphates or purine nucleotide 5'-diphosphates or purine nucleotide 5'-triphosphates. Particularly preferred novel proteins are those with subsequent modifications of the amino acid sequence and all combinations of amino acid sequence modifications which comprise these subsequent modifications.

Modifications of the amino acid sequence of the AgKPR1 gene product:
Lysine at position 7 replaced by valine
Aspartate at position 52 replaced by histidine
Leucine at position 119 replaced by isoleucine
Aspartate at position 186 replaced by histidine
Alanine at position 193 replaced by valine
Histidine at position 196 replaced by glutamine Modifications of the amino acid sequence of the AgADE4 gene product:
Aspartate at position 310 replaced by valine
Lysine at position 333 replaced by alanine
Alanine at position 417 replaced by tryptophan The following Examples describe the preparation of the novel proteins and nucleic acids and the use thereof for producing microorganisms with increased riboflavin synthesis.

EXAMPLE 1

Production of a Genomic Gene Bank from *Ashbya gossypii* ATCC10895

Genomic DNA from *Ashbya gossypii* ATCC10895 can be prepared by conventional methods as described, for example, in WO9703208. The genomic gene bank can be constructed starting from this DNA by conventional methods (e.g. Sambrook, J. et al. (1989) Molecular cloning: a laboratory manual, Cold Spring Harbor Laboratory Press or Ausubel, F. M. et al. (1994) Current protocols in molecular biology, John Wiley and sons) in any suitable plasmids or cosmids, such as, for example, SuperCos1 (Stratagene, La Jolla, USA).

EXAMPLE 2

Cloning of the Gene for PRPP Synthetase from *Ashbya gossypii* ATCC10895 (AgKPR1)

Cloning of the gene for PRPP synthetase from *Ashbya gossypii* (AgKPR1) can take place in two steps. In the first step, it is possible with the following oligonucleotides to amplify a defined region of the KPR1 gene from genomic DNA from *Ashbya gossypii* by PCR:

```
                                          (SEQ ID NO:14)
KPR5: 5'-GATGCTAGAGACCGCGGGGTGCAAC -3'

(SEQ ID NO:15)
KPR3: 5'-TGTCCGCCATGTCGTCTACAATAATA -3'
```

The PCR can be carried out by a conventional method. The resulting 330 bp DNA fragment can be cloned by conventional methods into the vector pGEMT (Promega, Madison, USA) and be sequenced.

A genomic cosmid gene bank can be screened by conventional methods using this nucleotide sequence as probe. A 1911 bp PstI-HindIII fragment of a cosmid which gives a signal with this probe can then be subcloned into the vector pbluescript SK+ (Stratagene, La Jolla, USA). The KPR1 gene and incomplete ORFs which show homology with the UBC6 and UBP9 genes of *Saccharomyces cerevisiae* are located on this fragment.

The PRPP synthetase KPR2 and the putative PRPP synthetase KPR4 from *Saccharomyces cerevisiae* are the enzymes which are most closely related, with similarities of 80.2% and 79.6% respectively, to the PRPP synthetase from *Ashbya gossypii*. The KPR2 and KPR4 genes from *Saccharomyces cerevisiae* have 67.6% and 67.8%, respectively, similarity with the KPR1 gene from *Ashbya gossypii*. Other enzymes and genes from other organisms are distinctly more different from the KPR1 gene and from the PRPP synthetase from *Ashbya gossypii*.

The sequence comparisons can be carried out, for example, with the Clustal algorithm with the aid of the PAM250 weighting table or the Wilbur-Lipman DNA alignment algorithm (as implemented, for example, in the MegAlign 3.06 program package supplied by DNAstar). It is not possible with the oligonucleotide pair described to amplify the genes for the different PRPP synthetases from *Saccharomyces cerevisiae*.

It is also possible to use the probe to find a further clone from the gene bank. This second clone showed a gene which likewise codes for a PRPP synthetase. This gene is called AgKPR2 and is distinctly different from AgKPR1. AgKPR2 shows 66% identity with AgKPR1 at the amino acid level. The AgKPR2 gene (SEQ ID NO:12) was compared with all proteins of the Swissprot database. The maximum similarity shown by this protein (88% identity and 95% similarity) is with the KPR3 gene product from *Saccharomyces cerevisiae*. The gene product of the AgKPR1 gene is responsible for the predominant part of the PRPP synthetase activity in *Ashbya gossypii*. Disruption of the AgKPR1 gene of *Ashbya gossypii* (analogous to the disruption of other *Ashbya* genes as in the descriptions in Examples 6–8) results in a distinctly reduced enzyme activity: in place of 22 U/mg of protein now only 3 U/mg of protein. See Example 13 for the analysis. Examples 11, 13 and 15 relate to the AgKPR1 gene, but studies of these types can also be carried out with AgKPR2.

EXAMPLE 3

Cloning of the Gene for Glutamine-PRPP Amidotransferase from *Ashbya gossypii* ATCC10895 (AgADE4)

The cloning of the gene for glutamine-PRPP amidotransferase from *Ashbya gossypii* (AgADE4) can take place in two steps.

In the first step, it is possible with the following oligonucleotides to amplify a defined region of the AgADE4 gene from genomic DNA of *Ashbya gossypii* by PCR:

```
                                      (SEQ ID NO:16)
ADE4A:  5'-ATATCTTGATGAAGACGTTCACCGT -3'

(SEQ ID NO:17)
ADE4B:  5'-GATAATGACGGCTTGGCCGGGAAGA -3'
```

The PCR can be carried out by a conventional method. The resulting 360 bp DNA fragment can be cloned by conventional methods into the vector pGEMT (Promega, Madison, USA) and then be sequenced.

This sequence can be used as probe to screen a genomic cosmid gene bank by conventional methods. It is then possible to subclone a 5369 bp HindIII fragment from a cosmid which gives a signal with this probe into the vector pBluescript SK+ (Stratagene, La Jolla, USA). The AgADE4 gene and the gene for the *Ashbya* homolog for the mitochondrial ABC transporter ATM1 from *Saccharomyces cerevisiae* and another open reading frame whose function is unknown are located on this fragment.

The AgADE4 gene product (glutamine-PRPP amidotransferase) shows the most evident similarity with the ADE4 gene products from *Saccharomyces cerevisiae* and *Saccharomyces kluyveri* (81% and 86.3% respectively). The corresponding genes show only 68.8% and 72%, respectively, homology, however. The similarity with other glutamine-PRPP amidotransferases is distinctly less (e.g. only 27.5% similarity with the corresponding enzyme from *Bacillus subtilis*). The sequence comparisons can be carried out as described in Example 2.

It is not possible with the described pair of oligonucleotides to amplify the ADE4 genes from *Saccharomyces cerevisiae* or *Saccharomyces kluyveri*.

EXAMPLE 4

Cloning of the Gene for Inosine-monophosphate Dehydrogenase from *Ashbya gossypii* ATCC10895 (AgGUA1)

Cloning of the gene for inosine-monophosphate dehydrogenase from *Ashbya gossypii* (AgGUA1) can take place in two steps.

In the first step, it is possible with the following oligonucleotides to amplify a defined region of the AgGUA1 gene from genomic DNA from *Ashbya gossypii* by PCR:

```
                                      (SEQ ID NO:18)
IMP5:  5'-GGCATCAACCTCGAGGAGGCGAACC -3'

(SEQ ID NO:19)
IMP3:  5'-CAGACCGGCCTCGACCAGCATCGCC -3'
```

The PCR can be carried out by a conventional method. The resulting 230 bp DNA fragment can be cloned by conventional methods into the vector pGEMT (Promega, Madison, USA) and then be sequenced.

This sequence can be used as probe to screen a genomic cosmid gene bank by conventional methods. A 3616 bp ApaI fragment from a cosmid which gives a signal with this probe can be subloned into the vector pBluescript SK+ (Stratagene, La Jolla, USA). The coding region of the AgGUA1 gene is 1569 bp long and is interrupted by a 161 bp-long intron. The intron boundaries (5' splice site AGG-TATGT and 3' splice site CAG) can be verified by cloning and sequencing of AgGUA1cDNA.

AgGUA1 is the first gene decribed from *Ashbya gossypii* having an intron.

The AgGUA1 gene product (IMP dehydrogenase) shows the most evident similarity with the 4 IMP dehydrogenases from *Saccharomyces cerevisiae* (similarities between 67% and 77.2%). The similarity with other IMP dehydrogenases is distinctly less. The sequence comparisons can be carried out as described in Example 2. *Ashbya gossypii* appears to have only one gene for this enzyme. This can be shown by Southern blotting with genomic DNA from *Ashbya gossypii* using the abovementioned probe.

The gene from *Saccharomyces cerevisiae* which codes for the IMP dehydrogenase (IMH3) which has most similarity with the AgGUA1 gene product has a similarity of 70.2% with the AgGUA1 gene. It is not possible with the described pair of oligonucleotides to amplify this gene from *Saccharomyces cerevisiae*.

EXAMPLE 5

Cloning of the Gene for Guanosine-monophosphate Synthetase from *Ashbya gossypii* ATCC10895 (AgGUA2)

Cloning of the gene for guanosine-monophosphate synthetase from *Ashbya gossypii* (AgGUA2) can take place in two steps.

In the first step, it is possible with the following oligonucleotides to amplify a defined region of the AgGUA2 gene from genomic DNA from *Ashbya gossypii* by PCR:

```
                                      (SEQ ID NO:20)
GUA2A:  5'-TGGACCGGGCGGTGTTCGAGTTGGG -3'

(SEQ ID NO:21)
GUA2B:  5'-AGGCTGGATCCTGGCTGCCTCGCGC -3'
```

The PCR can be carried out by a conventional method. The resulting 750 bp DNA fragment can be cloned by conventional methods into the vector pBluescript SK+ (Stratagene, La Jolla, USA) and then be sequenced.

This sequence can be used as probe to screen a genomic cosmid gene bank by conventional methods. A 2697 bp ClaI-EcoRV fragment from a cosmid which gives a signal with this probe can then be subcloned into the vector pBluescript SK+ (Stratagene, La Jolla, USA).

The AgGUA2 gene product (GMP synthetase) shows the most evident similarity with GMP synthetase from *Saccharomyces cerevisiae* (similarity 86.6%). The genes for the GMP synthetases from *Saccharomyces cerevisiae* and *Ashbya gossypii* show 71.2% homology. The similarity of the AgGUA2 gene product with other GMP synthetases is distinctly less. The sequence comparisons can be carried out as described in Example 2.

It is not possible with the described pair of oligonucleotides to amplify the GMP synthetase gene from *Saccharomyces cerevisiae*.

EXAMPLE 6

Disruption of the AgADE4 Gene from *Ashbya gossypii* ATCC10895

Disruption of a gene means destroying the functionality of a genomic copy of the gene either by (a) deleting part of the gene sequence, or by (b) interrupting the gene by inserting a piece of foreign DNA into the gene or by (c) replacing part of the gene by foreign DNA. Any foreign DNA can be used, but it is preferably a gene which brings about resistance to any suitable chemical. Any suitable resistance genes can be used for disruption of genes.

A gene which confers resistance to G418 can be used to disrupt the AgADE4 gene from *Ashbya gossypii* ATCC10895. It is possible for this to be the kanamycin resistance gene from TN903 under the control of the TEF promoter of *Ashbya gossypii* (see, for example, Yeast 10, pages 1793–1808, 1994, WO9200379). The gene is flanked 5' and 3' by several cleavage sites for restriction endonucleases, thus constructing a cassette which allows any desired constructions of gene disruptions by conventional methods of in vitro manipulation of DNA.

The internal HincII fragment of AgADE4 (between positions 2366 and 2924) can be replaced by a resistance cassette as outlined above. The resulting construct is called ade4::G418.

The resulting plasmid can be replicated in *E.coli*. The BamHI/BglII fragment of the construct ade4::G418 can be prepared, purified by agarose gel electrophoresis and subsequent elution of the DNA from the gel (see Proc. Natl. Acad. Sci. USA 76, 615–619, 1979) and employed for transforming *Ashbya gossypii*.

*Ashbya gossypii* can be transformed by protoplast transformation (Gene 109, 99–105, 1991), but preferably by electroporation (BioRad Gene Pulser, conditions: cuvettes with slit widths 0.4 mm, 1500V, 25 μF, 100Ω). Transformed cells are selected from G418-containing solid medium.

Resulting G418-resistant clones can be examined by conventional methods of PCR and Southern blot analysis to find whether the genomic copy of the AgADE4 gene is in fact destroyed. Clones whose AgADE4 gene is destroyed are purine-auxotrophic.

EXAMPLE 7

Disruption of the AgGUA1 Gene from *Ashbya gossypii* ATCC10895

See Example 6 for a description of the principle of disruption of genes, the use of a resistance cassette and the transformation of *Ashbya gossypii*.

The internal XhoI/KpnI fragment of AgGUA1 (between positions 1620 and 2061) can be replaced by a resistance cassette as outlined above. The resulting construct is called gua1::G418.

The resulting plasmid can be replicated in *E.coli*. The XbaI/BamHI fragment of the construct gua1::G418 can be prepared, purified by agarose gel electrophoresis and subsequent elution of the DNA from the gel and employed for transforming *Ashbya gossypii*.

Resulting G418-resistant clones can be examined by conventional methods of PCR and Southern blot analysis to find whether the genomic copy of the AgGUA1 gene is in fact destroyed. Clones whose AgGUA1 gene is destroyed are guanine-auxotrophic.

EXAMPLE 8

Disruption of the AgGUA2 Gene from *Ashbya gossypii* ATCC10895

See Example 6 for a description of the principle of disruption of genes, the use of a resistance cassette and the transformation of *Ashbya gossypii*.

The internal SalI fragment of AgGUA2 (between positions 1153 and 1219) can be replaced by a resistance cassette as outlined above. The resulting construct is called gua2::G418.

The resulting plasmid can be replicated in *E. coli*. The XbaI/BamHI fragment of the construct gua2::G418 can be prepared, purified by agarose gel electrophoresis and subsequent elution of the DNA from the gel and employed for transforming *Ashbya gossypii*.

Resulting G418-resistant clones can be examined by conventional methods of PCR and Southern blot analysis to find whether the genomic copy of the AgGUA2 gene is in fact destroyed. Clones whose AgGUA2 gene is destroyed are guanine-auxotrophic.

EXAMPLE 9

Cloning of the GAP Promoter from *Ashbya gossypii*

The gene for glyceraldehyde-3-phosphate dehydrogenase from *Ashbya gossypii* (AgGAP) can be cloned by generally customary screening of a genomic *Ashbya gossypii* cosmid gene bank (see Example 1, with a probe which was constructed from information on the sequence of the GAP gene from *Saccharomyces cerevisiae*).

The 5' nontranslated region of the gene (−373 to −8 region relative to the translation start) was assumed to be promoter. 2 cleavage sites for the restriction endonuclease NotI were inserted flanking this sequence. In this region there are the bona fide TATA Box (nt 224–230), two sequence sections (nt 43–51 and 77–85) which correspond to the GCR1 binding element, and a sequence section (nt 9–20) whose complement partially corresponds to the RAP1 binding element of *Saccharomyces cerevisiae* (see, for example, Johnston, M. and Carlson, M. (1992) pp. 193–281 in The molecular biology and cellular biology of the yeast *Saccharomyces*: Gene expression, Cold Spring Harbor Laboratory Press). The promoter cassette constructed in this way can be placed as easily portable expression signal in front of any desired gene for overexpression in *Ashbya gossypii* and results in pronounced overexpression of genes in *Ashbya gossypii*, as shown in Example 11.

EXAMPLE 10

Construction of Plasmids Having Genes Under the Control of the GAP Promoter from *Ashbya gossypii*

In order to introduce the GAP promoter cassette 5' of the coding region of the AgADE4 gene, a unique NotI cleavage site (recognition sequence GCGGCCGC) was inserted by conventional methods (e.g. Glover, D. M. and Hames, B. D. (1995) DNA cloning Vol.1, IRL press) 8 bp 5' of the ATG start codon.

The GAP promoter cassette can then be inserted via NotI into this position. An analogous procedure can be used for cloning the GAP promoter cassette 5' of the coding region of the genes AgKPR1, AgGUA1, AgGUA2 and for variants of the genes AgADE4, AgKPR1, AgGUA1 and AgGUA2.

Expression of the genes which harbor the GAP promoter cassette 5' of the coding region in *Ashbya gossypii* is controlled by the GAP promoter.

EXAMPLE 11

Overexpression of Genes in *Ashbya gossypii* Under the Control of the GAP Promoter Transformation of *Ashbya gossypii* with the DNA constructs described in Example 10 can be carried out as described in Example 6. The recipient clones can preferably, but not exclusively, be those which, before the transformation to be carried out here, harbor a disruption of the gene to be overexpressed. Thus, for example, the *Ashbya gossypii* mutant which is described in Example 6 and harbors an ade4::G418 mutation can be transformed with a GAP-ADE4 construct described in Example 10. Integration of the construct into the genome can be verified by Southern blot analysis. The resulting clones no longer have a G418 resistance gene (and are thus G418-sensitive) and are purine-prototrophic. Overexpression can be demonstrated by Northern blot analysis or detection of the enzymatic activity (as described in Example 12). On expression of the AgADE4 gene under the natural promoter, 0.007 U/mg of protein can be detected. On expression of the AgADE4 gene under the GAP promoter, 0.382 U/mg of protein can be detected.

A sequence section of the coding region of the AgADE4 gene can be used as probe. An analogous procedure can be used with AgKPR1, AgGUA1, AgGUA2 and for variants of all these genes. In addition, combinations of one of these genes together with other genes can be introduced in this way into the genome of *Ashbya gossypii*.

The wild type *Ashbya gossypii* has a specific PRPP synthetase activity of 22 U/mg of protein (see Example 13 for analysis of the PRPP synthetase). On expression of the AgKPR1 gene with the GAP promoter, 855 U/mg of protein is detectable.

EXAMPLE 12

Variants of the AgADE4 gene product (glutamine-PRPP amidotransferase) no longer subject to feedback inhibition by purines or intermediates of purine synthesis.

Glutamine-PRPP amidotransferases are subject to feedback inhibition by purine nucleotides. This inhibition is found in numerous organisms (see, for example, Switzer, R. L. (1989) Regulation of bacterial Glutamine Phosphoribosylpyrophosphate Amidotransferase, in: Allosteric enzymes pp. 129–151, CRC press, Boca Raton).

The glutamine-PRPP amidotransferase from *Ashbya gossypii* is likewise inhibited by AMP or GMP (see Figure). The activity of glutamine-phosphoribosyl-pyrophosphate amidotransferase from *Ashbya gossypii* can be measured as described in Messenger and Zalkin (1979) J. Biol. Chem. 254, pages 3382–3392.

Modified glutamine-phosphoribosyl-pyrophosphate amidotransferases no longer inhibited by purines can be constructed. It is evident that overexpression of such deregulated enzymes will enhance purine metabolism distinctly more than overexpression of enzymes subject to feedback inhibition. Alterations in the sequence of the AgADE4 gene can be brought about by conventional methods (e.g. Glover, D. M. and Hames, B. D. (1995) DNA cloning Vol.1, IRL press). It is possible, for example, for the following amino acids in glutamine-phosphoribosyl-pyrophosphate amidotransferase to be replaced:

The codon which codes for aspartate at position 310 can be replaced by a codon which codes for valine. The codon which codes for lysine at position 333 can be replaced by a codon which codes for alanine. The codon which codes for alanine at position 417 can be replaced by a codon which codes for tryptophan. It is additionally possible to construct AgADE4 genes which harbor combinations of these substitutions.

All enzymes which carry D310V, K333A, A417W or any combination of substitutions which comprise D310V or K333A show diminished feedback inhibition by AMP and GMP (see Figure). This can be shown, for example, by expressing the enzymes in *Ashbya gossypii* (see Example 11).

EXAMPLE 13

Variants of the AgKPR1 gene product (PRPP synthetase) no longer subject to feedback inhibition by purines or intermediates of purine synthesis.

PRPP synthetases are subject to feedback inhibition by purines, pyrimidines and amino acids. This inhibition is found in numerous organisms (see, for example, Gibson, K. J. et al. (1982) J. Biol. Chem. 257, 2391–2396; Tatibana, M. et al. (1995) Adv., Enzyme Regul. 35, 229–249 and papers quoted therein).

In clinical medical research there are descriptions of cases of hereditary gout based on enhanced purine biosynthesis. The molecular cause thereof is what is called superactivity of human PRPP synthetase (see, for example, Amer. J. Med. 55 (1973) 232–242; J. Clin. Invest. 96 (1995) 2133–2141; J. Biol. 268 (1993) 26476–26481). The basis thereof may be a mutation which leads to the enzyme no longer being subject to feedback inhibition by purines.

The activity of the PRPP synthetase from *Ashbya gossypii* can be measured as described in Anal. Biochem. 98 (1979) 254–263 or J. Bacteriol. 174 (1992) 6852–6856. The specific activity (U/mg) is defined via the amount of resulting product (nmol/min/g of protein).

It is possible to construct modified PRPP synthetases no longer inhibited by purines. It is evident that overexpression of such deregulated enzymes enhances purine metabolism distinctly more than does overexpression of enzymes subject to feedback inhibition. Modifications of the sequence of the AgKPR1 gene may be brought about by conventional methods (e.g. Glover, D. M. and Hames, B. D. (1995) DNA cloning Vol. 1, IRL press). It is possible, for example, to exchange the following amino acids of the PRPP synthetase:

The codon which codes for leucine at position 131 can be replaced by a codon which codes for isoleucine. The codon which codes for histidine at position 196 can be replaced by a codon which codes for glutamine.

All enzymes which have one of these amino acid exchanges (L131I or H196Q) show a reduced feedback inhibition by purines. FIG. 2 shows this by the example of ADP.

This can be shown after expression of the corresponding enzymes in *Ashbya gossypii*. This can be carried out in accordance with Example 11.

EXAMPLE 14

Variants of the AgGUA1 gene product (IMP dehydrogenase) no longer subject to feedback inhibition by purines or intermediates of purine synthesis.

EXAMPLE 15
Effects of the Enhancement and/or Optimization of Enzymes of Purine Metabolism and their Genes on Riboflavin Production in *Ashbya gossypii*

The original strain *Ashbya gossypii* ATCC10895 can be tested for riboflavin productivity in shaken flasks, comparing with clones which are derived therefrom and harbor chromosomal copies of genes under the control of the GAP promoter (as described in Example 11). It is possible to use for this purpose 300 ml shaken flasks with 20 ml of YPD medium (Sambrook, J. et al. (1989) Molecular cloning: a laboratory manual, Cold Spring Harbor Laboratory Press), incubating at a temperature of 28° C.

After 2 days, the control strain produces on average 14.5 mg of riboflavin per 1 of culture broth. Strains which overexpress genes for enzymes of purine metabolism (as shown, for example, in Example 11), or overexpress genes for optimized enzymes of purine metabolism (for example as in Examples 12, 13 and 14), produce more riboflavin. Thus, the strain which overexpresses AgADE4D310VK333A (Example 12) produces on average 45.4 mg of riboflavin per 1 of culture broth in 2 days.

The strain which overexpresses AgKPR1 with the GAP promoter produces not 14 mj/l (like the WT) but 36 mg/l riboflavin. The strain which overexpresses AgKPR1H196Q with the GAP promoter produces 51 mg/l riboflavin.

Figure 1:
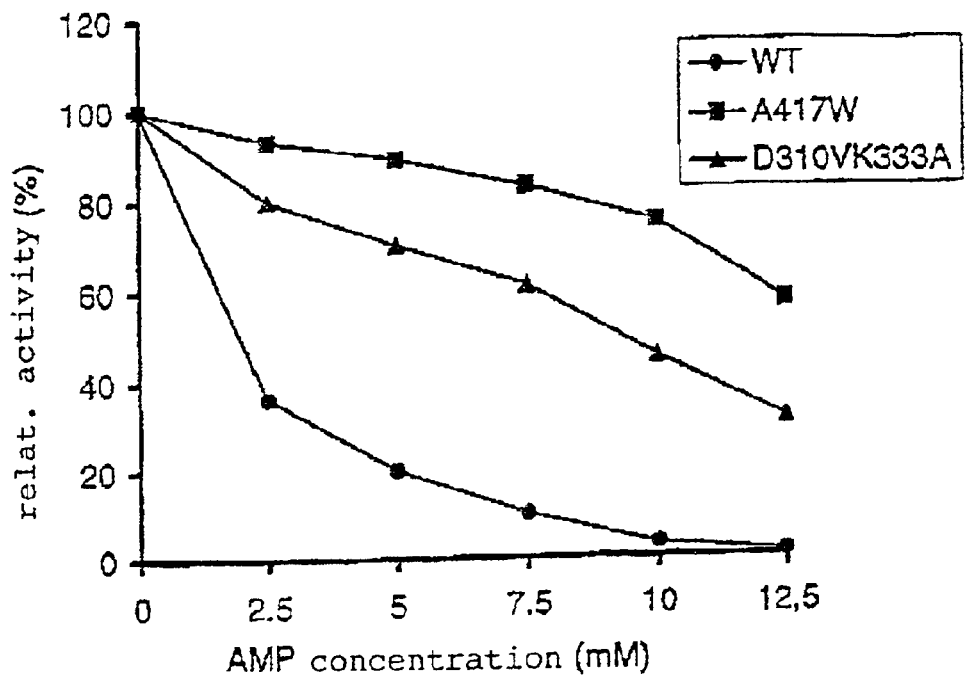
FIG. 1.
Figure 1:
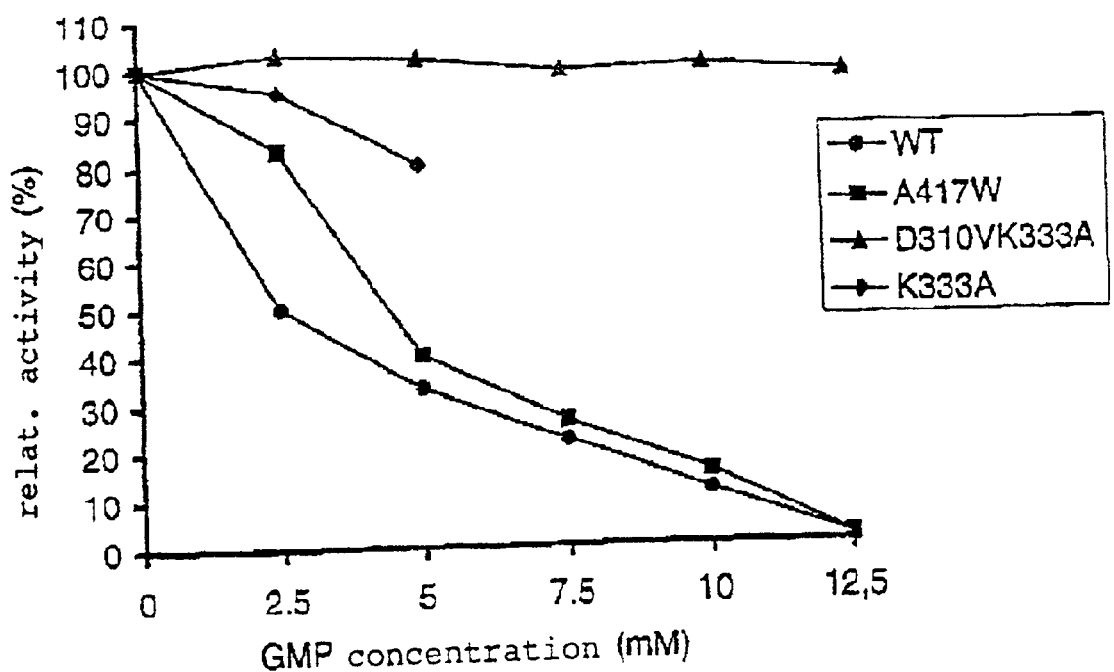
Figure 2:
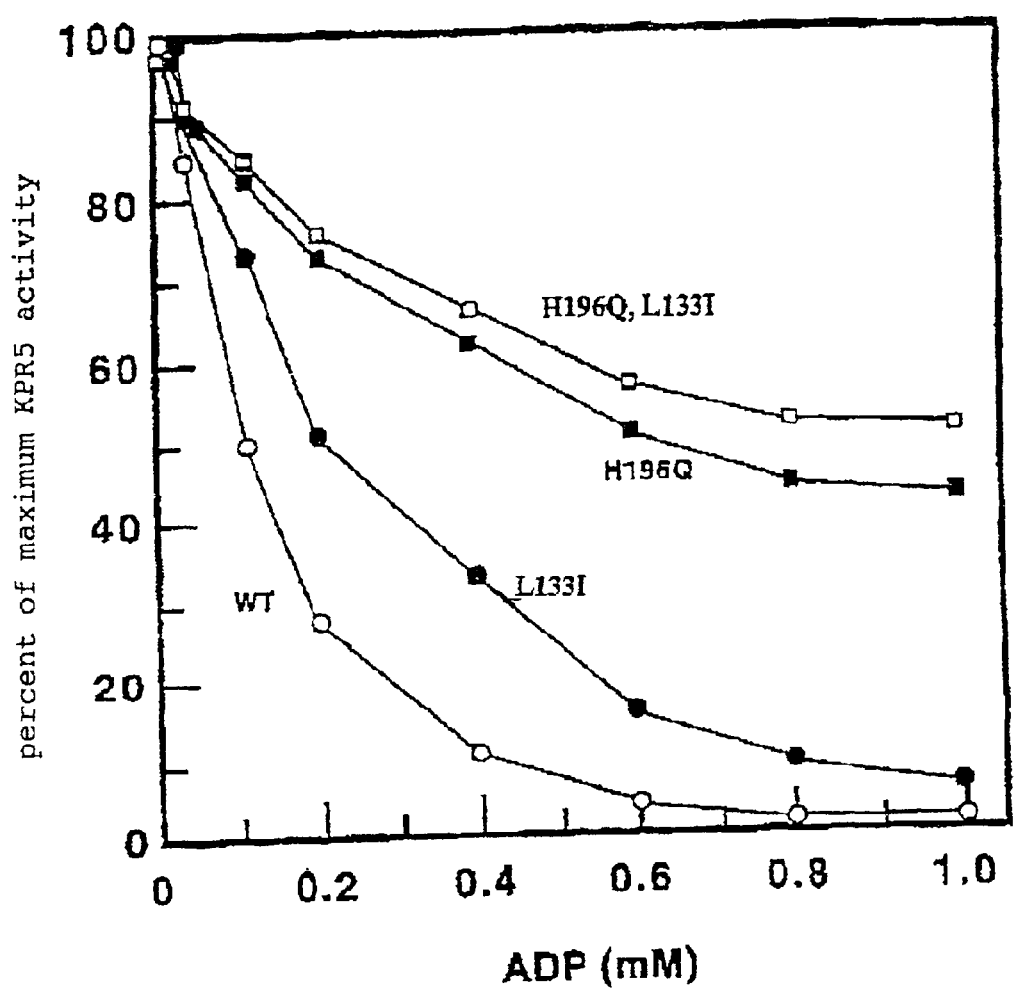

Measurement of the activity of Gln-PRPP amidotransferase from *A. gossypii* and of modified forms of the enzyme as a function of the concentration of adenosine 5'-monophosphate (AMP) and guanosine 5'-monophosphate (GMP).

WT: Gln-PRPP amidotransferase

A417W: Gln-PRPP amidotransferase, alanine at position 417 replaced by tryptophan.

K333A: Gln-PRPP amidotransferase, lysine at position 333 replaced by alanine.

D310VK333A: Gln-PRPP amidotransferase, aspartate at position 310 replaced by valine and lysine at position 333 replaced by alanine.

FIG. 2:

Measurement of the activity of the PRPP synthetase from *A. gossypii* and of modified forms of the enzyme as a function of the concentration of adenosine 5'-diphosphate (ADP)

WT: PRPP synthetase

L131I: PRPP synthetase, leucine at position 131 replaced by isoleucine

H196Q: PRPP synthetase, histidine at position 196 replaced by glutamine

H196Q, L131I: PRPP synthetase, histidine at position 196 replaced by glutamine and leucine at position 131 replaced by isoleucine

We claim:

1. A protein whose sequence differs from that set forth in SEQ ID NO: 2 in that lysine at position 7 is replaced by valine wherein said protein has the activity of a phosphoribosyl-pyrophosphate synthetase.

* * * * *

```
                        SEQUENCE LISTING

<160> NUMBER OF SEQ ID NOS: 21

<210> SEQ ID NO 1
<211> LENGTH: 1911
<212> TYPE: DNA
<213> ORGANISM: Ashbya gosypii
<220> FEATURE:
<221> NAME/KEY: CDS
<222> LOCATION: 626..1582

<400> SEQUENCE: 1
ggtagtcgct catcgacaga cacaatcgcg tgttctctct gaatcgtcca ttgggtgtca      60
gcatcctgat cgcgggcgga tggaatgggt aatcattagg aaacaccaat gtcccatggt     120
attgtccgtc ctcgtatggt gtctcaggag gacccgtgat cacgtagtgc cacaccagga     180
tattgtcttc ctttggtgct gccacgatgt agggcggggg gttctcggtc atcattttgt     240
actcctttga gagccgcttg tacgcctgtc ttgatgccat cttgcctact attagtttct     300
caccacttcc cgccaaacaa tctgcacttt acgagcgcta tctatccctc gggtcgctct     360
agttgattat tggcgaaact gatagttcag gtacttccat gatgcggtca tatccacgta     420
tgtgatcacg tgatcatcag ccatgctgcc agctcacggg cctgcctaca ctattggagg     480
ctctgtgagt catgatttat tgcatatcaa gcccagatag tcgttgggga tactaccgtt     540
gccgcgatga gctccgatat taagttgtag ccaaaaattt taacggatga cttcttaaca     600
gttattgacg ccgcaatcct acgcc atg tcg tcc aat agc ata aag ctg cta      652
                            Met Ser Ser Asn Ser Ile Lys Leu Leu
                                1               5 gca ggt aac tcg cac ccg gac cta gct gag aag gtc tcc gtt cgc cta      700
Ala Gly Asn Ser His Pro Asp Leu Ala Glu Lys Val Ser Val Arg Leu
```

-continued

```
        10              15              20              25
ggt gta cca ctt tcg aag att gga gtg tat cac tac tct aac aaa gag    748
Gly Val Pro Leu Ser Lys Ile Gly Val Tyr His Tyr Ser Asn Lys Glu
                30              35              40 acg tca gtt act atc ggc gaa agt atc cgt gat gaa gat gtc tac atc    796
Thr Ser Val Thr Ile Gly Glu Ser Ile Arg Asp Glu Asp Val Tyr Ile
            45              50              55 atc cag aca gga acg ggg gag cag gaa atc aac gac ttc ctc atg gaa    844
Ile Gln Thr Gly Thr Gly Glu Gln Glu Ile Asn Asp Phe Leu Met Glu
        60              65              70 ctg ctc atc atg atc cat gcc tgc cgg tca gcc tct gcg cgg aag atc    892
Leu Leu Ile Met Ile His Ala Cys Arg Ser Ala Ser Ala Arg Lys Ile
    75              80              85 aca gcg gtt ata cca aac ttc cct tac gca aga caa gac aaa aag gac    940
Thr Ala Val Ile Pro Asn Phe Pro Tyr Ala Arg Gln Asp Lys Lys Asp
90              95              100             105 aag tcg cga gca ccg ata act gcc aag ctg gtg gcc aag atg cta gag    988
Lys Ser Arg Ala Pro Ile Thr Ala Lys Leu Val Ala Lys Met Leu Glu
                110             115             120 acc gcg ggg tgc aac cac gtt atc acg atg gat ttg cac gcg tct caa    1036
Thr Ala Gly Cys Asn His Val Ile Thr Met Asp Leu His Ala Ser Gln
            125             130             135 att cag ggt ttc ttc cac att cca gtg gac aac cta tat gca gag ccg    1084
Ile Gln Gly Phe Phe His Ile Pro Val Asp Asn Leu Tyr Ala Glu Pro
        140             145             150 aac atc ctg cac tac atc caa cat aat gtg gac ttc cag aat agt atg    1132
Asn Ile Leu His Tyr Ile Gln His Asn Val Asp Phe Gln Asn Ser Met
    155             160             165 ttg gtc gcg cca gac gcg ggg tcg gcg aag cgc acg tcg acg ctt tcg    1180
Leu Val Ala Pro Asp Ala Gly Ser Ala Lys Arg Thr Ser Thr Leu Ser
170             175             180             185 gac aag ctg aat ctc aac ttc gcg ttg atc cac aaa gaa cgg cag aag    1228
Asp Lys Leu Asn Leu Asn Phe Ala Leu Ile His Lys Glu Arg Gln Lys
                190             195             200 gcg aac gag gtc tcg cgg atg gtg ttg gtg ggt gat gtc gcc gac aag    1276
Ala Asn Glu Val Ser Arg Met Val Leu Val Gly Asp Val Ala Asp Lys
            205             210             215 tcc tgt att att gta gac gac atg gcg gac acg tgc gga acg cta gtg    1324
Ser Cys Ile Ile Val Asp Asp Met Ala Asp Thr Cys Gly Thr Leu Val
        220             225             230 aag gcc act gac acg ctg atc gaa aat tgt gcg aaa gaa gtg att gcc    1372
Lys Ala Thr Asp Thr Leu Ile Glu Asn Cys Ala Lys Glu Val Ile Ala
    235             240             245 att gtg aca cac ggt ata ttt tct ggc ggc gcc cgc gag aag ttg cgc    1420
Ile Val Thr His Gly Ile Phe Ser Gly Gly Ala Arg Glu Lys Leu Arg
250             255             260             265 aac agc aag ctg gca cgg atc gta agc aca aat acg gtg cca gtg gac    1468
Asn Ser Lys Leu Ala Arg Ile Val Ser Thr Asn Thr Val Pro Val Asp
                270             275             280 ctc aat cta gat atc tac cac caa att gac att agt gcc att ttg gcc    1516
Leu Asn Leu Asp Ile Tyr His Gln Ile Asp Ile Ser Ala Ile Leu Ala
            285             290             295 gag gca att aga agg ctt cac aac ggg gaa agt gtg tcg tac ctg ttc    1564
Glu Ala Ile Arg Arg Leu His Asn Gly Glu Ser Val Ser Tyr Leu Phe
        300             305             310 aat aac gct gtc atg tagtgctgtc agtggcagat gcatgatcgc tggcctaatt    1619
Asn Asn Ala Val Met
    315 atctgtgtaa gttgatacaa tgcagtaaat acagtacata aaactgaatg tttttcactt    1679
```

```
agggggtgctt tgttgttctg atagcgtgtg tgcgaatttg gaggtgaaag ttgaacatca    1739
cgtaatgaat acaaacaaga ttgcacatta ggaaaagcga taaattattt attatttgca    1799
actggccttt gagcgtttaa gcctgaacat ttttgccctt ttgtttgacc gtaccgttat    1859
cactcgtcct tatatatggc tatccttctc ttccggaact tcttcgagcg ta            1911
```

<210> SEQ ID NO 2
<211> LENGTH: 318
<212> TYPE: PRT
<213> ORGANISM: Ashbya gosypii

<400> SEQUENCE: 2

```
Met Ser Ser Asn Ser Ile Lys Leu Leu Ala Gly Asn Ser His Pro Asp
  1               5                  10                  15

Leu Ala Glu Lys Val Ser Val Arg Leu Gly Val Pro Leu Ser Lys Ile
             20                  25                  30

Gly Val Tyr His Tyr Ser Asn Lys Glu Thr Ser Val Thr Ile Gly Glu
         35                  40                  45

Ser Ile Arg Asp Glu Asp Val Tyr Ile Ile Gln Thr Gly Thr Gly Glu
 50                  55                  60

Gln Glu Ile Asn Asp Phe Leu Met Glu Leu Leu Ile Met Ile His Ala
 65                  70                  75                  80

Cys Arg Ser Ala Ser Ala Arg Lys Ile Thr Ala Val Ile Pro Asn Phe
             85                  90                  95

Pro Tyr Ala Arg Gln Asp Lys Lys Asp Lys Ser Arg Ala Pro Ile Thr
            100                 105                 110

Ala Lys Leu Val Ala Lys Met Leu Glu Thr Ala Gly Cys Asn His Val
        115                 120                 125

Ile Thr Met Asp Leu His Ala Ser Gln Ile Gln Gly Phe Phe His Ile
130                 135                 140

Pro Val Asp Asn Leu Tyr Ala Glu Pro Asn Ile Leu His Tyr Ile Gln
145                 150                 155                 160

His Asn Val Asp Phe Gln Asn Ser Met Leu Val Ala Pro Asp Ala Gly
            165                 170                 175

Ser Ala Lys Arg Thr Ser Thr Leu Ser Asp Lys Leu Asn Leu Asn Phe
        180                 185                 190

Ala Leu Ile His Lys Glu Arg Gln Lys Ala Asn Glu Val Ser Arg Met
    195                 200                 205

Val Leu Val Gly Asp Val Ala Asp Lys Ser Cys Ile Ile Val Asp Asp
210                 215                 220

Met Ala Asp Thr Cys Gly Thr Leu Val Lys Ala Thr Asp Thr Leu Ile
225                 230                 235                 240

Glu Asn Cys Ala Lys Glu Val Ile Ala Ile Val Thr His Gly Ile Phe
            245                 250                 255

Ser Gly Gly Ala Arg Glu Lys Leu Arg Asn Ser Lys Leu Ala Arg Ile
        260                 265                 270

Val Ser Thr Asn Thr Val Pro Val Asp Leu Asn Leu Asp Ile Tyr His
    275                 280                 285

Gln Ile Asp Ile Ser Ala Ile Leu Ala Glu Ala Ile Arg Arg Leu His
290                 295                 300

Asn Gly Glu Ser Val Ser Tyr Leu Phe Asn Asn Ala Val Met
305                 310                 315
```

<210> SEQ ID NO 3

-continued

```
<211> LENGTH: 5369
<212> TYPE: DNA
<213> ORGANISM: Ashbya gossypii
<220> FEATURE:
<221> NAME/KEY: CDS
<222> LOCATION: 55..1482
<221> NAME/KEY: CDS
<222> LOCATION: 1767..3299
<221> NAME/KEY: CDS
<222> LOCATION: 3588..4703

<400> SEQUENCE: 3
```

| | | | | | | | | | | | | | | | | | |
|---|---|---|---|---|---|---|---|---|---|---|---|---|---|---|---|---|---|
| aagcttgacc | ttggctggca | cttgagtcgg | cagacaggtg | gactaacccg | agca | atg | | | | | | | | | | | 57 |
| | | | | | | Met | | | | | | | | | | | |
| | | | | | | 1 | | | | | | | | | | | |

| gat | cgt | ggt | tgt | aaa | ggt | atc | tct | tat | gtg | ctc | agt | gca | atg | gtt | ttt | 105 |
|---|---|---|---|---|---|---|---|---|---|---|---|---|---|---|---|---|
| Asp | Arg | Gly | Cys | Lys | Gly | Ile | Ser | Tyr | Val | Leu | Ser | Ala | Met | Val | Phe | |
| | | | 5 | | | | | 10 | | | | | 15 | | | |

| cac | ata | ata | ccg | att | aca | ttt | gaa | ata | tcg | atg | gta | tgt | ggc | ata | ttg | 153 |
|---|---|---|---|---|---|---|---|---|---|---|---|---|---|---|---|---|
| His | Ile | Ile | Pro | Ile | Thr | Phe | Glu | Ile | Ser | Met | Val | Cys | Gly | Ile | Leu | |
| | | 20 | | | | | 25 | | | | | 30 | | | | |

| aca | tac | cag | ttt | ggt | gct | tcc | ttc | gct | gct | ata | aca | ttc | tcg | act | atg | 201 |
|---|---|---|---|---|---|---|---|---|---|---|---|---|---|---|---|---|
| Thr | Tyr | Gln | Phe | Gly | Ala | Ser | Phe | Ala | Ala | Ile | Thr | Phe | Ser | Thr | Met | |
| | 35 | | | | | 40 | | | | | 45 | | | | | |

| ctt | ctt | tac | tcc | atc | ttt | act | ttc | aga | acg | acg | gcg | tgg | cgc | aca | cgg | 249 |
|---|---|---|---|---|---|---|---|---|---|---|---|---|---|---|---|---|
| Leu | Leu | Tyr | Ser | Ile | Phe | Thr | Phe | Arg | Thr | Thr | Ala | Trp | Arg | Thr | Arg | |
| 50 | | | | | 55 | | | | | 60 | | | | | 65 | |

| ttt | agg | cgt | gat | gcg | aac | aag | gct | gac | aat | aag | gcc | gct | agt | gtg | gca | 297 |
|---|---|---|---|---|---|---|---|---|---|---|---|---|---|---|---|---|
| Phe | Arg | Arg | Asp | Ala | Asn | Lys | Ala | Asp | Asn | Lys | Ala | Ala | Ser | Val | Ala | |
| | | | 70 | | | | | 75 | | | | | 80 | | | |

| ttg | gat | tcc | cta | ata | aat | ttt | gaa | gct | gta | aag | tat | ttc | aat | aac | gag | 345 |
|---|---|---|---|---|---|---|---|---|---|---|---|---|---|---|---|---|
| Leu | Asp | Ser | Leu | Ile | Asn | Phe | Glu | Ala | Val | Lys | Tyr | Phe | Asn | Asn | Glu | |
| | | 85 | | | | | 90 | | | | | 95 | | | | |

| aag | tac | ctt | gcg | gac | aag | tat | cac | aca | tcc | ttg | atg | aag | tac | cgg | gat | 393 |
|---|---|---|---|---|---|---|---|---|---|---|---|---|---|---|---|---|
| Lys | Tyr | Leu | Ala | Asp | Lys | Tyr | His | Thr | Ser | Leu | Met | Lys | Tyr | Arg | Asp | |
| | 100 | | | | | 105 | | | | | 110 | | | | | |

| tcc | cag | ata | aag | gtc | tcg | caa | tcg | ctg | gcg | ttt | ttg | aac | acc | ggc | cag | 441 |
|---|---|---|---|---|---|---|---|---|---|---|---|---|---|---|---|---|
| Ser | Gln | Ile | Lys | Val | Ser | Gln | Ser | Leu | Ala | Phe | Leu | Asn | Thr | Gly | Gln | |
| 115 | | | | | 120 | | | | | 125 | | | | | | |

| aac | cta | att | ttt | acc | act | gca | ctg | act | gca | atg | atg | tat | atg | gcc | tgt | 489 |
|---|---|---|---|---|---|---|---|---|---|---|---|---|---|---|---|---|
| Asn | Leu | Ile | Phe | Thr | Thr | Ala | Leu | Thr | Ala | Met | Met | Tyr | Met | Ala | Cys | |
| 130 | | | | | 135 | | | | | 140 | | | | | 145 | |

| aat | ggt | gtt | atg | cag | ggc | tct | ctt | aca | gtg | ggg | gat | ctt | gtg | tta | att | 537 |
|---|---|---|---|---|---|---|---|---|---|---|---|---|---|---|---|---|
| Asn | Gly | Val | Met | Gln | Gly | Ser | Leu | Thr | Val | Gly | Asp | Leu | Val | Leu | Ile | |
| | | | 150 | | | | | 155 | | | | | 160 | | | |

| aat | caa | ctg | gta | ttc | cag | ctc | tcc | gtg | cca | cta | aac | ttc | ctt | ggt | agc | 585 |
|---|---|---|---|---|---|---|---|---|---|---|---|---|---|---|---|---|
| Asn | Gln | Leu | Val | Phe | Gln | Leu | Ser | Val | Pro | Leu | Asn | Phe | Leu | Gly | Ser | |
| | | | 165 | | | | | 170 | | | | | 175 | | | |

| gtc | tac | cgt | gat | ctc | aag | cag | tct | ctg | ata | gat | atg | gaa | tct | tta | ttt | 633 |
|---|---|---|---|---|---|---|---|---|---|---|---|---|---|---|---|---|
| Val | Tyr | Arg | Asp | Leu | Lys | Gln | Ser | Leu | Ile | Asp | Met | Glu | Ser | Leu | Phe | |
| | | 180 | | | | | 185 | | | | | 190 | | | | |

| aaa | ctg | caa | aaa | aat | cag | gtc | aca | att | aag | aac | tcc | cca | aat | gcc | cag | 681 |
|---|---|---|---|---|---|---|---|---|---|---|---|---|---|---|---|---|
| Lys | Leu | Gln | Lys | Asn | Gln | Val | Thr | Ile | Lys | Asn | Ser | Pro | Asn | Ala | Gln | |
| 195 | | | | | 200 | | | | | 205 | | | | | | |

| aac | cta | cca | ata | cac | aaa | ccg | ttg | gat | att | cgc | ttt | gaa | aat | gtt | acg | 729 |
|---|---|---|---|---|---|---|---|---|---|---|---|---|---|---|---|---|
| Asn | Leu | Pro | Ile | His | Lys | Pro | Leu | Asp | Ile | Arg | Phe | Glu | Asn | Val | Thr | |
| 210 | | | | 215 | | | | | 220 | | | | | 225 | | |

| ttt | ggc | tat | gac | ccg | gag | cgg | cgt | ata | ttg | aac | aat | gtt | tcg | ttt | acc | 777 |
|---|---|---|---|---|---|---|---|---|---|---|---|---|---|---|---|---|
| Phe | Gly | Tyr | Asp | Pro | Glu | Arg | Arg | Ile | Leu | Asn | Asn | Val | Ser | Phe | Thr | |
| | | | 230 | | | | | 235 | | | | | 240 | | | |

| atc | cca | gct | gga | atg | aag | act | gcc | ata | gta | ggc | cca | tcg | ggc | tcg | ggg | 825 |
|---|---|---|---|---|---|---|---|---|---|---|---|---|---|---|---|---|
| Ile | Pro | Ala | Gly | Met | Lys | Thr | Ala | Ile | Val | Gly | Pro | Ser | Gly | Ser | Gly | |

```
                                -continued
         245              250              255
aag tcc acc att ttg aag ctc gta ttt aga ttc tat gag ccc gag caa      873
Lys Ser Thr Ile Leu Lys Leu Val Phe Arg Phe Tyr Glu Pro Glu Gln
        260              265              270 ggt cgt atc cta gtt ggc ggc aca gat atc cgc gat tta gac ttg ctt      921
Gly Arg Ile Leu Val Gly Gly Thr Asp Ile Arg Asp Leu Asp Leu Leu
    275              280              285 tct tta cgg aag gct atc ggt gtc gtg ccc caa gat act cct ctc ttc      969
Ser Leu Arg Lys Ala Ile Gly Val Val Pro Gln Asp Thr Pro Leu Phe
290             295              300              305 aat gac aca atc tgg gag aat gtt aaa ttc ggc aat atc agt tcc tct     1017
Asn Asp Thr Ile Trp Glu Asn Val Lys Phe Gly Asn Ile Ser Ser Ser
                310              315              320 gac gat gag att ctc agg gcc ata gaa aaa gct caa ctc acg aag cta     1065
Asp Asp Glu Ile Leu Arg Ala Ile Glu Lys Ala Gln Leu Thr Lys Leu
            325              330              335 ctc cag aac cta cca aag ggc gct tcc acc gtt gta ggg gag cgc ggt     1113
Leu Gln Asn Leu Pro Lys Gly Ala Ser Thr Val Val Gly Glu Arg Gly
        340              345              350 ttg atg atc agc gga ggt gag aaa caa agg ctt gct att gct cgt gtg     1161
Leu Met Ile Ser Gly Gly Glu Lys Gln Arg Leu Ala Ile Ala Arg Val
    355              360              365 ctt ttg aag gac gct ccg ctg atg ttt ttc gac gag gct aca agt gct     1209
Leu Leu Lys Asp Ala Pro Leu Met Phe Phe Asp Glu Ala Thr Ser Ala
370             375              380              385 ctg gat aca cac aca gag cag gca ctc ttg cac acc att cag cag aac     1257
Leu Asp Thr His Thr Glu Gln Ala Leu Leu His Thr Ile Gln Gln Asn
                390              395              400 ttt tct tcc aat tca aag acg agc gtt tac gtt gcc cat aga ctg cgc     1305
Phe Ser Ser Asn Ser Lys Thr Ser Val Tyr Val Ala His Arg Leu Arg
            405              410              415 aca atc gct gat gca gat aag atc att gtt ctt gaa caa ggt tct gtc     1353
Thr Ile Ala Asp Ala Asp Lys Ile Ile Val Leu Glu Gln Gly Ser Val
        420              425              430 cgc gaa gag ggc aca cac agc tcg ctg tta gcg tca caa gga tcc cta     1401
Arg Glu Glu Gly Thr His Ser Ser Leu Leu Ala Ser Gln Gly Ser Leu
    435              440              445 tac cgg ggt ctg tgg gat att cag gaa aac cta acg ctt ccg gaa cgg     1449
Tyr Arg Gly Leu Trp Asp Ile Gln Glu Asn Leu Thr Leu Pro Glu Arg
450             455              460              465 cct gag cag tca acc gga tct cag cat gca tagacgtctg actagagatt      1499
Pro Glu Gln Ser Thr Gly Ser Gln His Ala
                470              475 atataataac cctcgagcca aaattatacg gcgctaacaa gtaaaatttt agttacttt    1559 tctgacttct ctacgctgac ttctctaccc ttctaacata gttaattgaa gtagtggtta   1619
atgacgactg cattttatta ttgtccactt tgcattagaa gtactagtgc ttaagcgctc   1679
tttaggccgc tttcttcttc tttgtcaggc cgcaaggtaa aggaagcacc aacgattgc    1739 taccgctgct attcctgctc tctcaag atg tgt ggc ata tta ggc gtt gtg       1790
                            Met Cys Gly Ile Leu Gly Val Val
                                                    480 cta gcc gat cag tcg aag gtg gtc gcc cct gag ttg ttt gat ggc tca     1838
Leu Ala Asp Gln Ser Lys Val Val Ala Pro Glu Leu Phe Asp Gly Ser
            485              490              495 ctg ttc tta cag cat cgc ggt caa gat gct gcc ggg att gct acg tgc     1886
Leu Phe Leu Gln His Arg Gly Gln Asp Ala Ala Gly Ile Ala Thr Cys
500             505              510              515 ggc ccc ggt ggg cgc ttg tac caa tgt aag ggc aat ggt atg gca cgg     1934
```

| | | |
|---|---|---|
| Gly Pro Gly Gly Arg Leu Tyr Gln Cys Lys Gly Asn Gly Met Ala Arg<br>520 525 530 | | |
| gac gtg ttc acg caa gct cgg atg tca ggg ttg gtt ggc tct atg ggg<br>Asp Val Phe Thr Gln Ala Arg Met Ser Gly Leu Val Gly Ser Met Gly<br>535 540 545 | | 1982 |
| att gca cac ctg aga tat ccc act gca ggc tcc agt gcg aac tca gaa<br>Ile Ala His Leu Arg Tyr Pro Thr Ala Gly Ser Ser Ala Asn Ser Glu<br>550 555 560 | | 2030 |
| gcg cag cca ttc tat gtg aat agt ccc tac gga att tgc atg agt cat<br>Ala Gln Pro Phe Tyr Val Asn Ser Pro Tyr Gly Ile Cys Met Ser His<br>565 570 575 | | 2078 |
| aat ggt aat ctg gtg aac acg atg tct cta cgt aga tat ctt gat gaa<br>Asn Gly Asn Leu Val Asn Thr Met Ser Leu Arg Arg Tyr Leu Asp Glu<br>580 585 590 595 | | 2126 |
| gac gtt cac cgt cat att aac acg gac agc gat tct gag cta ctg ctt<br>Asp Val His Arg His Ile Asn Thr Asp Ser Asp Ser Glu Leu Leu Leu<br>600 605 610 | | 2174 |
| aat ata ttt gcc gcg gag ctg gaa aag tac aac aaa tat cgt gtg aac<br>Asn Ile Phe Ala Ala Glu Leu Glu Lys Tyr Asn Lys Tyr Arg Val Asn<br>615 620 625 | | 2222 |
| aac gat gat ata ttt tgt gct cta gag ggt gtt tac aaa cgt tgt cgc<br>Asn Asp Asp Ile Phe Cys Ala Leu Glu Gly Val Tyr Lys Arg Cys Arg<br>630 635 640 | | 2270 |
| ggt ggc tat gct tgt gtt ggc atg ttg gcg gga tat gga ttg ttt ggt<br>Gly Gly Tyr Ala Cys Val Gly Met Leu Ala Gly Tyr Gly Leu Phe Gly<br>645 650 655 | | 2318 |
| ttc cgg gac ccc aat ggg atc agg ccg cta ttg ttt ggt gag cgc gtc<br>Phe Arg Asp Pro Asn Gly Ile Arg Pro Leu Leu Phe Gly Glu Arg Val<br>660 665 670 675 | | 2366 |
| aac gat gac ggc acc atg gac tac atg cta gcg tcc gaa agt gtc gtt<br>Asn Asp Asp Gly Thr Met Asp Tyr Met Leu Ala Ser Glu Ser Val Val<br>680 685 690 | | 2414 |
| ctt aag gcc cac cgc ttc caa aac ata cgt gat att ctt ccc ggc caa<br>Leu Lys Ala His Arg Phe Gln Asn Ile Arg Asp Ile Leu Pro Gly Gln<br>695 700 705 | | 2462 |
| gcc gtc att atc cct aaa acg tgc ggc tcc agt cca cca gag ttc cgg<br>Ala Val Ile Ile Pro Lys Thr Cys Gly Ser Ser Pro Pro Glu Phe Arg<br>710 715 720 | | 2510 |
| cag gta gtg cca att gag gcc tac aaa ccg gac ttg ttt gag tac gtg<br>Gln Val Val Pro Ile Glu Ala Tyr Lys Pro Asp Leu Phe Glu Tyr Val<br>725 730 735 | | 2558 |
| tat ttc gct cgt gct gac agc gtt ctg gac ggt att tcc gtt tac cat<br>Tyr Phe Ala Arg Ala Asp Ser Val Leu Asp Gly Ile Ser Val Tyr His<br>740 745 750 755 | | 2606 |
| aca cgc ctg ttg atg ggt atc aaa ctt gcc gag aac atc aaa aaa cag<br>Thr Arg Leu Leu Met Gly Ile Lys Leu Ala Glu Asn Ile Lys Lys Gln<br>760 765 770 | | 2654 |
| atc gat ctg gac gaa att gac gtt gtt gta tct gtt cct gac act gca<br>Ile Asp Leu Asp Glu Ile Asp Val Val Val Ser Val Pro Asp Thr Ala<br>775 780 785 | | 2702 |
| cgt acc tgt gca ttg gag tgt gcc aac cat tta aac aaa cct tat cgc<br>Arg Thr Cys Ala Leu Glu Cys Ala Asn His Leu Asn Lys Pro Tyr Arg<br>790 795 800 | | 2750 |
| gaa gga ttt gtc aag aac aga tat gtt gga aga aca ttt atc atg cca<br>Glu Gly Phe Val Lys Asn Arg Tyr Val Gly Arg Thr Phe Ile Met Pro<br>805 810 815 | | 2798 |
| aac caa aaa gag cga gta tct tct gtg cgc cgc aag ttg aac cca atg<br>Asn Gln Lys Glu Arg Val Ser Ser Val Arg Arg Lys Leu Asn Pro Met<br>820 825 830 835 | | 2846 |

```
aac tca gaa ttt aaa gac aag cgc gtg ctg att gtc gat gat tcc att        2894
Asn Ser Glu Phe Lys Asp Lys Arg Val Leu Ile Val Asp Asp Ser Ile
                840                 845                 850 gtg cga ggt acc act tcc aaa gag att gtt aac atg gcg aag gaa tcc        2942
Val Arg Gly Thr Thr Ser Lys Glu Ile Val Asn Met Ala Lys Glu Ser
            855                 860                 865 ggt gct gcc aag gtc tac ttt gcc tct gca gcg cca gca att cgt ttc        2990
Gly Ala Ala Lys Val Tyr Phe Ala Ser Ala Ala Pro Ala Ile Arg Phe
        870                 875                 880 aat cac atc tac ggg att gac cta gca gat act aag cag ctt gtc gcc        3038
Asn His Ile Tyr Gly Ile Asp Leu Ala Asp Thr Lys Gln Leu Val Ala
    885                 890                 895 tac aac aga act gtt gaa gaa atc act gcg gag ctg ggc tgt gac cgc        3086
Tyr Asn Arg Thr Val Glu Glu Ile Thr Ala Glu Leu Gly Cys Asp Arg
900                 905                 910                 915 gtc atc tat caa tct ttg gat gac ctc atc gac tgt tgc aag aca gac        3134
Val Ile Tyr Gln Ser Leu Asp Asp Leu Ile Asp Cys Cys Lys Thr Asp
                920                 925                 930 atc atc tca gaa ttt gaa gtt gga gtt ttc act ggt aac tac gtt aca        3182
Ile Ile Ser Glu Phe Glu Val Gly Val Phe Thr Gly Asn Tyr Val Thr
            935                 940                 945 ggt gtt gag gat gtg tac ttg cag gaa tta gaa cgt tgc cgc gct ctt        3230
Gly Val Glu Asp Val Tyr Leu Gln Glu Leu Glu Arg Cys Arg Ala Leu
        950                 955                 960 aat aac tcg aat aag ggt gaa gcg aag gcc gag gtt gat att ggt ctc        3278
Asn Asn Ser Asn Lys Gly Glu Ala Lys Ala Glu Val Asp Ile Gly Leu
    965                 970                 975 tac aat tct gcc gac tat tagcggcgcc gttgccggca tccggcccca              3326
Tyr Asn Ser Ala Asp Tyr
980                 985 tatatagact catcgggacc taaaataagc ctttacagat cattatctac aaatatagat      3386
accattaaaa gcctgacttt cgacttactc ctagcacacc ccgttgtatc cctgtgcttg      3446
ctttcttaaa tgccgttggt taggctttgg acttagcgtc ccgcccattt tctagcatgt      3506
gcagatctag caaatttggc ctaagacaag aagatccatt cggcacccac atcctggagc      3566
cagcacacag tggacccaga c atg agc agc ggc aat ata tgg aag caa ttg        3617
              Met Ser Ser Gly Asn Ile Trp Lys Gln Leu
                                      990                 995 cta gag gag aat agc gaa cag ctg gac cag tcc act acg gag act tac        3665
Leu Glu Glu Asn Ser Glu Gln Leu Asp Gln Ser Thr Thr Glu Thr Tyr
            1000                1005                1010 gtg gta tgc tgc gag aac gaa gat tcc ctt aac cag ttt ttg caa caa        3713
Val Val Cys Cys Glu Asn Glu Asp Ser Leu Asn Gln Phe Leu Gln Gln
        1015                1020                1025 tgt tgg cag att gac gag ggc gag aag gtg acc aac ctg gag ccg ttg        3761
Cys Trp Gln Ile Asp Glu Gly Glu Lys Val Thr Asn Leu Glu Pro Leu
    1030                1035                1040 gga ttc ttt aca aag gtg gtt tcg cgc gac gaa gag aac ctc cgg ctc        3809
Gly Phe Phe Thr Lys Val Val Ser Arg Asp Glu Glu Asn Leu Arg Leu
1045                1050                1055 aac gta tac tat gcc aag agc cca ctg gat gca cag acg ctg cag ttt        3857
Asn Val Tyr Tyr Ala Lys Ser Pro Leu Asp Ala Gln Thr Leu Gln Phe
                1060                1065                1075 ctg ggt gtg ttc ctg cgc caa atg gaa acc tca caa ata cgt tgg atc        3905
Leu Gly Val Phe Leu Arg Gln Met Glu Thr Ser Gln Ile Arg Trp Ile
            1080                1085                1090 ttc cta ctg gac tgg ctg cta gac gat aaa cga tta tgg cta cgt caa        3953
Phe Leu Leu Asp Trp Leu Leu Asp Asp Lys Arg Leu Trp Leu Arg Gln
        1095                1100                1105
```

```
ctg cgg aac tcg tgg gcc gcc ttg gag gaa gcg cag gtg gca ccc ttt        4001
Leu Arg Asn Ser Trp Ala Ala Leu Glu Glu Ala Gln Val Ala Pro Phe
        1110                1115                1120 cca ggt ggc gct gtg gtg gtg gtc ctc aac ccg agt cac gtg aca caa        4049
Pro Gly Gly Ala Val Val Val Val Leu Asn Pro Ser His Val Thr Gln
    1125                1130                1135 ctg gag cga aac acg atg gtt tgg aac tcc cgc cgt ctg gac ctg gta        4097
Leu Glu Arg Asn Thr Met Val Trp Asn Ser Arg Arg Leu Asp Leu Val
1140                1145                1150                1155 cac cag aca ctg cga gct gca tgc ctc aac acc ggc tcg gcg cta gtt        4145
His Gln Thr Leu Arg Ala Ala Cys Leu Asn Thr Gly Ser Ala Leu Val
            1160                1165                1170 aca ctt gat cct aat act gcg cgc gaa gac gtc atg cac ata tgt gcg        4193
Thr Leu Asp Pro Asn Thr Ala Arg Glu Asp Val Met His Ile Cys Ala
        1175                1180                1185 ctg ctt gcg ggg ctg cct aca tcc cgt ccc gtc gcg atg cta agc ctg        4241
Leu Leu Ala Gly Leu Pro Thr Ser Arg Pro Val Ala Met Leu Ser Leu
    1190                1195                1200 caa agt cta ttc atc ccc cac ggt gca gat tcc atc ggc aag atc tgc        4289
Gln Ser Leu Phe Ile Pro His Gly Ala Asp Ser Ile Gly Lys Ile Cys
1205                1210                1215 acc atc gcg ccc gag ttc cct gtt gct acg gtg ttc gac aac gat ttt        4337
Thr Ile Ala Pro Glu Phe Pro Val Ala Thr Val Phe Asp Asn Asp Phe
1220                1225                1230                1235 gtg agc tcg aca ttc gag gcc gca att gct cca gaa ctt act cca gga        4385
Val Ser Ser Thr Phe Glu Ala Ala Ile Ala Pro Glu Leu Thr Pro Gly
            1240                1245                1250 cca cgt gtg cca tct gac cac cca tgg cta aca gag cct acc aac ccc        4433
Pro Arg Val Pro Ser Asp His Pro Trp Leu Thr Glu Pro Thr Asn Pro
        1255                1260                1265 cct tcg gag gca acc gct tgg cat ttc gat ctc caa ggt cgc ctc gct        4481
Pro Ser Glu Ala Thr Ala Trp His Phe Asp Leu Gln Gly Arg Leu Ala
    1270                1275                1280 acc cta tac cgg cat ctt ggt gac tct aac aag gcc ata tct gtt act        4529
Thr Leu Tyr Arg His Leu Gly Asp Ser Asn Lys Ala Ile Ser Val Thr
1285                1290                1295 cag cac cgc ttc cac aag ccc cgc tcg gaa gat tat gca tac gaa ttc        4577
Gln His Arg Phe His Lys Pro Arg Ser Glu Asp Tyr Ala Tyr Glu Phe
1300                1305                1310                1315 gag ctg ccg tct aag cac cct aca ata cgt gac ctc ata cgc tct gcc        4625
Glu Leu Pro Ser Lys His Pro Thr Ile Arg Asp Leu Ile Arg Ser Ala
            1320                1325                1330 gca gcc gac tca ccg aac gac gtc gct gac tcc atc gat ggg ctt atg        4673
Ala Ala Asp Ser Pro Asn Asp Val Ala Asp Ser Ile Asp Gly Leu Met
        1335                1340                1345 gat ggt atc gta caa agg aat gtt cat tgacgtcgac acaaaaattt              4720
Asp Gly Ile Val Gln Arg Asn Val His
    1350                1355 tgttactgtt ctctcgagaa ctattctcat ccagtactga catattagaa ggcgaagtga     4780
actaggattt atataaagta gccttcaggc aattgcacag ggtctattga gtcgctgccg     4840
ttcacgagag agcccaatat atcgaggact aattggtcac ttttgttttg ctatactcac     4900
cctgtatttg ctaatcattt atccgctttg tccaagtggt tgcgaagata tcgagccaga    4960
acattagaat ctggtttgcc gcatcctaga gctgtctcca agccagttga accgttgcgg    5020
gagattaccg cagccggttt gatcagagta ctggtgactg ccagcaccca cgtttgtgac    5080 ttataaaatat acgccctgtg gagccatagc cattggcata aagagaagag caccccgtgc   5140
```

-continued

```
cacgatgcag acacttccgg tgtacccagc gtcacagact gcgtcgccta cgaagcgtga    5200
acttgcagcg gcgccctcgg tgccgcagga cggcgcccgg ctgcctgcgc agctcacttt    5260
agtgacgccc ccagaacctg atatccagaa gaagtcagtg cgatctcagg tcgcgcgttt    5320
aagcatctcg gagacagatg tagtgaagag tgatatcgtg gctaagctt               5369
```

<210> SEQ ID NO 4
<211> LENGTH: 475
<212> TYPE: PRT
<213> ORGANISM: Asbya gossypii

<400> SEQUENCE: 4

```
Met Asp Arg Gly Cys Lys Gly Ile Ser Tyr Val Leu Ser Ala Met Val
 1               5                  10                  15

Phe His Ile Ile Pro Ile Thr Phe Glu Ile Ser Met Val Cys Gly Ile
             20                  25                  30

Leu Thr Tyr Gln Phe Gly Ala Ser Phe Ala Ala Ile Thr Phe Ser Thr
         35                  40                  45

Met Leu Leu Tyr Ser Ile Phe Thr Phe Arg Thr Thr Ala Trp Arg Thr
     50                  55                  60

Arg Phe Arg Arg Asp Ala Asn Lys Ala Asp Asn Lys Ala Ala Ser Val
 65                  70                  75                  80

Ala Leu Asp Ser Leu Ile Asn Phe Glu Ala Val Lys Tyr Phe Asn Asn
                 85                  90                  95

Glu Lys Tyr Leu Ala Asp Lys Tyr His Thr Ser Leu Met Lys Tyr Arg
            100                 105                 110

Asp Ser Gln Ile Lys Val Ser Gln Ser Leu Ala Phe Leu Asn Thr Gly
        115                 120                 125

Gln Asn Leu Ile Phe Thr Thr Ala Leu Thr Ala Met Met Tyr Met Ala
    130                 135                 140

Cys Asn Gly Val Met Gln Gly Ser Leu Thr Val Gly Asp Leu Val Leu
145                 150                 155                 160

Ile Asn Gln Leu Val Phe Gln Leu Ser Val Pro Leu Asn Phe Leu Gly
                165                 170                 175

Ser Val Tyr Arg Asp Leu Lys Gln Ser Leu Ile Asp Met Glu Ser Leu
            180                 185                 190

Phe Lys Leu Gln Lys Asn Gln Val Thr Ile Lys Asn Ser Pro Asn Ala
        195                 200                 205

Gln Asn Leu Pro Ile His Lys Pro Leu Asp Ile Arg Phe Glu Asn Val
    210                 215                 220

Thr Phe Gly Tyr Asp Pro Glu Arg Arg Ile Leu Asn Asn Val Ser Phe
225                 230                 235                 240

Thr Ile Pro Ala Gly Met Lys Thr Ala Ile Val Gly Pro Ser Gly Ser
                245                 250                 255

Gly Lys Ser Thr Ile Leu Lys Leu Val Phe Arg Phe Tyr Glu Pro Glu
            260                 265                 270

Gln Gly Arg Ile Leu Val Gly Gly Thr Asp Ile Arg Asp Leu Asp Leu
        275                 280                 285

Leu Ser Leu Arg Lys Ala Ile Gly Val Val Pro Gln Asp Thr Pro Leu
    290                 295                 300

Phe Asn Asp Thr Ile Trp Glu Asn Val Lys Phe Gly Asn Ile Ser Ser
305                 310                 315                 320

Ser Asp Asp Glu Ile Leu Arg Ala Ile Glu Lys Ala Gln Leu Thr Lys
                325                 330                 335
```

```
Leu Leu Gln Asn Leu Pro Lys Gly Ala Ser Thr Val Val Gly Glu Arg
                340                 345                 350

Gly Leu Met Ile Ser Gly Gly Glu Lys Gln Arg Leu Ala Ile Ala Arg
            355                 360                 365

Val Leu Leu Lys Asp Ala Pro Leu Met Phe Phe Asp Glu Ala Thr Ser
        370                 375                 380

Ala Leu Asp Thr His Thr Glu Gln Ala Leu Leu His Thr Ile Gln Gln
385                 390                 395                 400

Asn Phe Ser Ser Asn Ser Lys Thr Ser Val Tyr Val Ala His Arg Leu
                405                 410                 415

Arg Thr Ile Ala Asp Ala Asp Lys Ile Ile Val Leu Glu Gln Gly Ser
            420                 425                 430

Val Arg Glu Glu Gly Thr His Ser Ser Leu Leu Ala Ser Gln Gly Ser
        435                 440                 445

Leu Tyr Arg Gly Leu Trp Asp Ile Gln Glu Asn Leu Thr Leu Pro Glu
    450                 455                 460

Arg Pro Glu Gln Ser Thr Gly Ser Gln His Ala
465                 470                 475

<210> SEQ ID NO 5
<211> LENGTH: 510
<212> TYPE: PRT
<213> ORGANISM: Ashbya gossypii

<400> SEQUENCE: 5

Met Cys Gly Ile Leu Gly Val Val Leu Ala Asp Gln Ser Lys Val Val
1               5                   10                  15

Ala Pro Glu Leu Phe Asp Gly Ser Leu Phe Leu Gln His Arg Gly Gln
            20                  25                  30

Asp Ala Ala Gly Ile Ala Thr Cys Gly Pro Gly Gly Arg Leu Tyr Gln
        35                  40                  45

Cys Lys Gly Asn Gly Met Ala Arg Asp Val Phe Thr Gln Ala Arg Met
    50                  55                  60

Ser Gly Leu Val Gly Ser Met Gly Ile Ala His Leu Arg Tyr Pro Thr
65                  70                  75                  80

Ala Gly Ser Ser Ala Asn Ser Glu Ala Gln Pro Phe Tyr Val Asn Ser
                85                  90                  95

Pro Tyr Gly Ile Cys Met Ser His Asn Gly Asn Leu Val Asn Thr Met
            100                 105                 110

Ser Leu Arg Arg Tyr Leu Asp Glu Asp Val His Arg His Ile Asn Thr
        115                 120                 125

Asp Ser Asp Ser Glu Leu Leu Leu Asn Ile Phe Ala Ala Glu Leu Glu
    130                 135                 140

Lys Tyr Asn Lys Tyr Arg Val Asn Asn Asp Ile Phe Cys Ala Leu
145                 150                 155                 160

Glu Gly Val Tyr Lys Arg Cys Arg Gly Gly Tyr Ala Cys Val Gly Met
                165                 170                 175

Leu Ala Gly Tyr Gly Leu Phe Gly Phe Arg Asp Pro Asn Gly Ile Arg
            180                 185                 190

Pro Leu Leu Phe Gly Glu Arg Val Asn Asp Gly Thr Met Asp Tyr
        195                 200                 205

Met Leu Ala Ser Glu Ser Val Val Leu Lys Ala His Arg Phe Gln Asn
    210                 215                 220

Ile Arg Asp Ile Leu Pro Gly Gln Ala Val Ile Ile Pro Lys Thr Cys
225                 230                 235                 240
```

-continued

```
Gly Ser Ser Pro Pro Glu Phe Arg Gln Val Val Pro Ile Glu Ala Tyr
                245                 250                 255

Lys Pro Asp Leu Phe Glu Tyr Val Tyr Phe Ala Arg Ala Asp Ser Val
            260                 265                 270

Leu Asp Gly Ile Ser Val Tyr His Thr Arg Leu Leu Met Gly Ile Lys
        275                 280                 285

Leu Ala Glu Asn Ile Lys Lys Gln Ile Asp Leu Asp Glu Ile Asp Val
    290                 295                 300

Val Val Ser Val Pro Asp Thr Ala Arg Thr Cys Ala Leu Glu Cys Ala
305                 310                 315                 320

Asn His Leu Asn Lys Pro Tyr Arg Glu Gly Phe Val Lys Asn Arg Tyr
            325                 330                 335

Val Gly Arg Thr Phe Ile Met Pro Asn Gln Lys Glu Arg Val Ser Ser
        340                 345                 350

Val Arg Arg Lys Leu Asn Pro Met Asn Ser Glu Phe Lys Asp Lys Arg
    355                 360                 365

Val Leu Ile Val Asp Asp Ser Ile Val Arg Gly Thr Thr Ser Lys Glu
370                 375                 380

Ile Val Asn Met Ala Lys Glu Ser Gly Ala Ala Lys Val Tyr Phe Ala
385                 390                 395                 400

Ser Ala Ala Pro Ala Ile Arg Phe Asn His Ile Tyr Gly Ile Asp Leu
            405                 410                 415

Ala Asp Thr Lys Gln Leu Val Ala Tyr Asn Arg Thr Val Glu Glu Ile
        420                 425                 430

Thr Ala Glu Leu Gly Cys Asp Arg Val Ile Tyr Gln Ser Leu Asp Asp
    435                 440                 445

Leu Ile Asp Cys Cys Lys Thr Asp Ile Ile Ser Glu Phe Glu Val Gly
    450                 455                 460

Val Phe Thr Gly Asn Tyr Val Thr Gly Val Glu Asp Val Tyr Leu Gln
465                 470                 475                 480

Glu Leu Glu Arg Cys Arg Ala Leu Asn Ser Asn Lys Gly Glu Ala
            485                 490                 495

Lys Ala Glu Val Asp Ile Gly Leu Tyr Asn Ser Ala Asp Tyr
        500                 505                 510
```

<210> SEQ ID NO 6
<211> LENGTH: 371
<212> TYPE: PRT
<213> ORGANISM: Ashbya gossypii

<400> SEQUENCE: 6

```
Met Ser Ser Gly Asn Ile Trp Lys Gln Leu Leu Glu Glu Asn Ser Glu
  1               5                  10                  15

Gln Leu Asp Gln Ser Thr Thr Glu Thr Tyr Val Val Cys Cys Glu Asn
            20                  25                  30

Glu Asp Ser Leu Asn Gln Phe Leu Gln Gln Cys Trp Gln Ile Asp Glu
        35                  40                  45

Gly Glu Lys Val Thr Asn Leu Glu Pro Leu Gly Phe Phe Thr Lys Val
    50                  55                  60

Val Ser Arg Asp Glu Glu Asn Leu Arg Leu Asn Val Tyr Tyr Ala Lys
65                  70                  75                  80

Ser Pro Leu Asp Ala Gln Thr Leu Gln Phe Leu Gly Val Phe Leu Arg
                85                  90                  95

Gln Met Glu Thr Ser Gln Ile Arg Trp Ile Phe Leu Leu Asp Trp Leu
```

-continued

```
                100              105                110
Leu Asp Asp Lys Arg Leu Trp Leu Arg Gln Leu Arg Asn Ser Trp Ala
        115                 120                 125
Ala Leu Glu Glu Ala Gln Val Ala Pro Phe Pro Gly Gly Ala Val Val
        130                 135                 140
Val Val Leu Asn Pro Ser His Val Thr Gln Leu Glu Arg Asn Thr Met
145                 150                 155                 160
Val Trp Asn Ser Arg Arg Leu Asp Leu Val His Gln Thr Leu Arg Ala
                165                 170                 175
Ala Cys Leu Asn Thr Gly Ser Ala Leu Val Thr Leu Asp Pro Asn Thr
            180                 185                 190
Ala Arg Glu Asp Val Met His Ile Cys Ala Leu Leu Ala Gly Leu Pro
            195                 200                 205
Thr Ser Arg Pro Val Ala Met Leu Ser Leu Gln Ser Leu Phe Ile Pro
            210                 215                 220
His Gly Ala Asp Ser Ile Gly Lys Ile Cys Thr Ile Ala Pro Glu Phe
225                 230                 235                 240
Pro Val Ala Thr Val Phe Asp Asn Asp Phe Val Ser Ser Thr Phe Glu
                245                 250                 255
Ala Ala Ile Ala Pro Glu Leu Thr Pro Gly Pro Arg Val Pro Ser Asp
            260                 265                 270
His Pro Trp Leu Thr Glu Pro Thr Asn Pro Pro Ser Glu Ala Thr Ala
            275                 280                 285
Trp His Phe Asp Leu Gln Gly Arg Leu Ala Thr Leu Tyr Arg His Leu
            290                 295                 300
Gly Asp Ser Asn Lys Ala Ile Ser Val Thr Gln His Arg Phe His Lys
305                 310                 315                 320
Pro Arg Ser Glu Asp Tyr Ala Tyr Glu Phe Glu Leu Pro Ser Lys His
                325                 330                 335
Pro Thr Ile Arg Asp Leu Ile Arg Ser Ala Ala Ala Asp Ser Pro Asn
            340                 345                 350
Asp Val Ala Asp Ser Ile Asp Gly Leu Met Asp Gly Ile Val Gln Arg
            355                 360                 365
Asn Val His
    370
```

<210> SEQ ID NO 7
<211> LENGTH: 3616
<212> TYPE: DNA
<213> ORGANISM: Ashbya gossypii
<220> FEATURE:
<221> NAME/KEY: CDS
<222> LOCATION: 864..1316
<221> NAME/KEY: CDS
<222> LOCATION: 1478..2592

<400> SEQUENCE: 7

| | | |
|---|---|---|
| gggcccggtg ccagctcgcc aggtgcggac tcgcgctcgg gctgtgggcg ctctacctgc | 60 |
| tgctgctcgg cagctgcctg acgcgcgcgt acgagctgtc ggatctcgaa aacctggaat | 120 |
| ccgattacta cagctacgtg ctggatgtga acttcgcgct gctgagcgcc atgagcgcga | 180 |
| ccggcctcgc gatgggcgcc gtgagcggct ccctcgggag cgcgccggtg ctcgcgcagt | 240 |
| ggccggcagc gatctgggcc gtgcgcttcc tgcgcgccgc gggctatgtc gcgatagtcc | 300 |
| taatcctgcc gttcctgtcc gtcgtcgcat tcctgcagcc gctctgcgag cgcgcgctgg | 360 |
| cgctgttccc gtttgtgcgc gcgtggggca tggacggcgt gttcaacttc ctgctgctct | 420 |

```
ccgccgtgct ctggactgta ttcctggccg ttcgcctgct ccgcgccgtc tacagactgc    480
tgcgctggct ggtcggtctt ttggtccgcc tggcacgcct gctgctgcga ggcgcccgtc    540
ggacgcctgc ggcggccccc gaggagcccg tctagcgtgc gcgcgttcta ggcccctgac    600
agctcctacc tggtgctggc cgccggtagg gctcgcatcg tgcggcgcag gcccattgct    660
ttttggcccc cgctggatca tcgtttcttt tacgtgaaaa gtttgcagcg atgagctgca    720
gtataaatag gttttctaga tgcgccaaat cccagctggg tttaccggcg tctgttcggg    780
atagttactt gatggatggg tcaacttgag agcttgggtt tagtgttgac tccttctctt    840
catagcacgc cgaacaaagc gca atg act tac aga gac gca gcc acg gca       890
                         Met Thr Tyr Arg Asp Ala Ala Thr Ala
                          1               5
```

```
ctg gag cac ctg gcg acg tac gcc gag aag gac ggg ctg tcc gtg gag     938
Leu Glu His Leu Ala Thr Tyr Ala Glu Lys Asp Gly Leu Ser Val Glu
 10              15                  20                  25 cag ttg atg gac tcc aag acg cgg ggc ggg ttg acg tac aac gac ttc     986
Gln Leu Met Asp Ser Lys Thr Arg Gly Gly Leu Thr Tyr Asn Asp Phe
             30                  35                  40 ctg gtc ttg ccg ggc aag atc gac ttc cca tcg tcg gag gtg gtg ctg    1034
Leu Val Leu Pro Gly Lys Ile Asp Phe Pro Ser Ser Glu Val Val Leu
         45                  50                  55 tcg tcg cgc ctg acc aag aag atc acc ttg aac gcg ccg ttt gtg tcg    1082
Ser Ser Arg Leu Thr Lys Lys Ile Thr Leu Asn Ala Pro Phe Val Ser
     60                  65                  70 tcg ccg atg gac acg gtg acg gag gcc gac atg gcg atc cac atg gcg    1130
Ser Pro Met Asp Thr Val Thr Glu Ala Asp Met Ala Ile His Met Ala
 75                  80                  85 ctc ctg ggc ggc atc ggg atc atc cac cac aac tgc act gcg gag gag    1178
Leu Leu Gly Gly Ile Gly Ile Ile His His Asn Cys Thr Ala Glu Glu
 90                  95                 100                 105 cag gcg gag atg gtg cgc cgg gtc aag aag tac gaa aac ggg ttc atc    1226
Gln Ala Glu Met Val Arg Arg Val Lys Lys Tyr Glu Asn Gly Phe Ile
                110                 115                 120 aac gcc ccc gtg gtc gtg ggg ccg gac gcg acg gtg gcg gac gtg cgc    1274
Asn Ala Pro Val Val Val Gly Pro Asp Ala Thr Val Ala Asp Val Arg
            125                 130                 135 cgg atg aag aac gag ttt ggg ttt gca gga ttt cct gtg aca            1316
Arg Met Lys Asn Glu Phe Gly Phe Ala Gly Phe Pro Val Thr
        140                 145                 150 ggtatgttag agtggcacgc ggggctgcac gctgggatga tgatcataaa tcaataactt   1376
tcgttctact gactgcgatc aaacgatcgt gtagacacct tttactctga ccgcagacgt   1436
gcagcgcctt tttggcagga acatgtacta acacatcagc a gat gat ggc aag      1489
                                             Asp Asp Gly Lys
                                                         155 ccg acc ggg aag ctg cag ggg atc atc acg tcc cgt gac atc cag ttt    1537
Pro Thr Gly Lys Leu Gln Gly Ile Ile Thr Ser Arg Asp Ile Gln Phe
                160                 165                 170 gtc gag gac gag acc ctg ctt gtg tct gag atc atg acc aag gac gtc    1585
Val Glu Asp Glu Thr Leu Leu Val Ser Glu Ile Met Thr Lys Asp Val
        175                 180                 185 atc act ggg aag cag ggc atc aac ctc gag gag gcg aac cag atc ctg    1633
Ile Thr Gly Lys Gln Gly Ile Asn Leu Glu Glu Ala Asn Gln Ile Leu
    190                 195                 200 aag aac acc aag aag ggc aag ctg cca att gtg gac gag gcg ggc tgc    1681
Lys Asn Thr Lys Lys Gly Lys Leu Pro Ile Val Asp Glu Ala Gly Cys
205                 210                 215
```

```
                                              -continued
ctg gtg tcc atg ctt tcg aga act gac ttg atg aag aac cag tcc tac    1729
Leu Val Ser Met Leu Ser Arg Thr Asp Leu Met Lys Asn Gln Ser Tyr
220                 225                 230                 235 cca ttg gcc tcc aag tct gcc gac acc aag cag ctg ctc tgt ggt gct    1777
Pro Leu Ala Ser Lys Ser Ala Asp Thr Lys Gln Leu Leu Cys Gly Ala
            240                 245                 250 gcg atc ggc acc atc gac gcg gac agg cag aga ctg gcg atg ctg gtc    1825
Ala Ile Gly Thr Ile Asp Ala Asp Arg Gln Arg Leu Ala Met Leu Val
        255                 260                 265 gag gcc ggt ctg gac gtt gtt gtg cta gac tcc tcg cag ggt aac tcg    1873
Glu Ala Gly Leu Asp Val Val Val Leu Asp Ser Ser Gln Gly Asn Ser
    270                 275                 280 gtc ttc cag atc aac atg atc aag tgg atc aag gag acc ttc cca gac    1921
Val Phe Gln Ile Asn Met Ile Lys Trp Ile Lys Glu Thr Phe Pro Asp
285                 290                 295 ctg cag gtc att gct ggc aac gtg gtc acc aga gag cag gct gcc agc    1969
Leu Gln Val Ile Ala Gly Asn Val Val Thr Arg Glu Gln Ala Ala Ser
300                 305                 310                 315 ttg atc cac gcc ggc gca gac ggg ttg cgt atc ggt atg ggc tct ggc    2017
Leu Ile His Ala Gly Ala Asp Gly Leu Arg Ile Gly Met Gly Ser Gly
            320                 325                 330 tcc atc tgt atc act cag gag gtg atg gcc tgt ggt aga cca cag ggt    2065
Ser Ile Cys Ile Thr Gln Glu Val Met Ala Cys Gly Arg Pro Gln Gly
        335                 340                 345 acc gct gtc tac aac gtc acg cag ttc gcc aac cag ttt ggt gtg cca    2113
Thr Ala Val Tyr Asn Val Thr Gln Phe Ala Asn Gln Phe Gly Val Pro
    350                 355                 360 tgt att gct gac ggt ggt gtc cag aac atc ggg cac att acc aaa gct    2161
Cys Ile Ala Asp Gly Gly Val Gln Asn Ile Gly His Ile Thr Lys Ala
365                 370                 375 atc gct ctt ggc gcg tcc acc gtc atg atg ggc ggt atg ctg gca ggc    2209
Ile Ala Leu Gly Ala Ser Thr Val Met Met Gly Gly Met Leu Ala Gly
380                 385                 390                 395 act aca gag tct cca ggc gag tac ttc ttc agg gac ggg aag aga ctg    2257
Thr Thr Glu Ser Pro Gly Glu Tyr Phe Phe Arg Asp Gly Lys Arg Leu
            400                 405                 410 aag acc tac aga ggt atg ggc tcc atc gac gcc atg caa aag act gat    2305
Lys Thr Tyr Arg Gly Met Gly Ser Ile Asp Ala Met Gln Lys Thr Asp
        415                 420                 425 gtc aag ggt aac gcc gct acc tcc cgt tac ttc tct gag tct gac aag    2353
Val Lys Gly Asn Ala Ala Thr Ser Arg Tyr Phe Ser Glu Ser Asp Lys
    430                 435                 440 gtt ctg gtc gct cag ggt gtt act ggt tct gtg atc gac aag ggc tcc    2401
Val Leu Val Ala Gln Gly Val Thr Gly Ser Val Ile Asp Lys Gly Ser
445                 450                 455 atc aag aag tac att cca tat ctg tac aat ggt cta cag cac tcg tgc    2449
Ile Lys Lys Tyr Ile Pro Tyr Leu Tyr Asn Gly Leu Gln His Ser Cys
460                 465                 470                 475 cag gat atc ggt gtg cgc tct cta gtg gag ttc aga gag aag gtg gac    2497
Gln Asp Ile Gly Val Arg Ser Leu Val Glu Phe Arg Glu Lys Val Asp
            480                 485                 490 tct ggc tcg gtc aga ttt gag ttc aga act cca tct gcc cag ttg gag    2545
Ser Gly Ser Val Arg Phe Glu Phe Arg Thr Pro Ser Ala Gln Leu Glu
        495                 500                 505 ggt ggt gtg cac aac ttg cac tcc tac gag aag cgc cta ttt gactgagtgc 2597
Gly Gly Val His Asn Leu His Ser Tyr Glu Lys Arg Leu Phe Asp
    510                 515                 520 cactaggccc acactataga agtggatccg ggcgcgatgg cacccatact tttatattat   2657
gttgattgat gtacgtaaac gatagatata ataacagacg cggcatctca tttgtatgca   2717
```

| | | | |
|---|---|---|---|
| atatatctgg | aacatggtta | tgcgtactca | actgtatgta ctactttata tacacagctc | 2777 |
| tgggacactt | ggtgagatat | atgtttcatt | atgtatgcct cgctatcgaa aggtctggca | 2837 |
| ttatgggcta | ctgggtctaa | gagtcatggc | ttatgagtat ttatttattt atttctcttc | 2897 |
| cttttcatta | aactcctcga | gcttctttct | gtaatactgc tctctagact tctccacatc | 2957 |
| tgctaatgat | ggtggaagtc | gttcgttttc | caaatccgct ctacgagcgc gctcgaagtt | 3017 |
| agacagcgcc | tcgttcagac | cttcagaccc | gcgtgacagc gctccacgag cagcacgcc | 3077 |
| agaattcatt | gttttaggt | actgcacctt | atcgctctct tctctcaaca cgctatacat | 3137 |
| tcgggaaacc | ttggcaatcg | ccaatatttt | actgcgtagt gcacgccgtt ttgcatcatc | 3197 |
| gtccagaata | gaccgttttt | tcttcgattt | cttggagcca ggtataacag ttacaacctg | 3257 |
| ctcagtgttt | ttggacttca | atgtagcacc | taagtcctcc cttataacaa aagtctcttc | 3317 |
| ctccaattct | tcttcagtac | aaatgtttaa | tatcgaaacc aacatttcag tcactttctc | 3377 |
| gccaacaaat | ggcaaagacc | aggtgaatac | gtccatgaaa ttcggtaacc aatacggatg | 3437 |
| ctgtgacatg | ttaaattgtc | taatgttcat | aacgttatcc gagtatttta ggaccgcggc | 3497 |
| cttgttcttg | taagtgtcca | agtagttggg | tgcgctgaac aacgtaagta aactaggaaa | 3557 |
| gcccagattc | ttggtattct | tgtacattct | gtagccctga tcttgggctt cgtgggccc | 3616 |

<210> SEQ ID NO 8
<211> LENGTH: 151
<212> TYPE: PRT
<213> ORGANISM: Ashbya gossypii

<400> SEQUENCE: 8

Met Thr Tyr Arg Asp Ala Ala Thr Ala Leu Glu His Leu Ala Thr Tyr
1               5                   10                  15

Ala Glu Lys Asp Gly Leu Ser Val Glu Gln Leu Met Asp Ser Lys Thr
            20                  25                  30

Arg Gly Gly Leu Thr Tyr Asn Asp Phe Leu Val Leu Pro Gly Lys Ile
        35                  40                  45

Asp Phe Pro Ser Ser Glu Val Val Leu Ser Ser Arg Leu Thr Lys Lys
    50                  55                  60

Ile Thr Leu Asn Ala Pro Phe Val Ser Ser Pro Met Asp Thr Val Thr
65                  70                  75                  80

Glu Ala Asp Met Ala Ile His Met Ala Leu Leu Gly Gly Ile Gly Ile
                85                  90                  95

Ile His His Asn Cys Thr Ala Glu Glu Gln Ala Glu Met Val Arg Arg
            100                 105                 110

Val Lys Lys Tyr Glu Asn Gly Phe Ile Asn Ala Pro Val Val Val Gly
        115                 120                 125

Pro Asp Ala Thr Val Ala Asp Val Arg Arg Met Lys Asn Glu Phe Gly
    130                 135                 140

Phe Ala Gly Phe Pro Val Thr
145                 150

<210> SEQ ID NO 9
<211> LENGTH: 371
<212> TYPE: PRT
<213> ORGANISM: Ashbya gossypii

<400> SEQUENCE: 9

Asp Asp Gly Lys Pro Thr Gly Lys Leu Gln Gly Ile Ile Thr Ser Arg
1               5                   10                  15

```
Asp Ile Gln Phe Val Glu Asp Glu Thr Leu Leu Val Ser Glu Ile Met
            20                  25                  30

Thr Lys Asp Val Ile Thr Gly Lys Gln Gly Ile Asn Leu Glu Glu Ala
        35                  40                  45

Asn Gln Ile Leu Lys Asn Thr Lys Gly Lys Leu Pro Ile Val Asp
    50                  55                  60

Glu Ala Gly Cys Leu Val Ser Met Leu Ser Arg Thr Asp Leu Met Lys
65                  70                  75                  80

Asn Gln Ser Tyr Pro Leu Ala Ser Lys Ser Ala Asp Thr Lys Gln Leu
                85                  90                  95

Leu Cys Gly Ala Ala Ile Gly Thr Ile Asp Ala Asp Arg Gln Arg Leu
            100                 105                 110

Ala Met Leu Val Glu Ala Gly Leu Asp Val Val Leu Asp Ser Ser
        115                 120                 125

Gln Gly Asn Ser Val Phe Gln Ile Asn Met Ile Lys Trp Ile Lys Glu
    130                 135                 140

Thr Phe Pro Asp Leu Gln Val Ile Ala Gly Asn Val Val Thr Arg Glu
145                 150                 155                 160

Gln Ala Ala Ser Leu Ile His Ala Gly Ala Asp Gly Leu Arg Ile Gly
                165                 170                 175

Met Gly Ser Gly Ser Ile Cys Ile Thr Gln Glu Val Met Ala Cys Gly
            180                 185                 190

Arg Pro Gln Gly Thr Ala Val Tyr Asn Val Thr Gln Phe Ala Asn Gln
        195                 200                 205

Phe Gly Val Pro Cys Ile Ala Asp Gly Gly Val Gln Asn Ile Gly His
    210                 215                 220

Ile Thr Lys Ala Ile Ala Leu Gly Ala Ser Thr Val Met Met Gly Gly
225                 230                 235                 240

Met Leu Ala Gly Thr Thr Glu Ser Pro Gly Glu Tyr Phe Phe Arg Asp
                245                 250                 255

Gly Lys Arg Leu Lys Thr Tyr Arg Gly Met Gly Ser Ile Asp Ala Met
            260                 265                 270

Gln Lys Thr Asp Val Lys Gly Asn Ala Ala Thr Ser Arg Tyr Phe Ser
        275                 280                 285

Glu Ser Asp Lys Val Leu Val Ala Gln Gly Val Thr Gly Ser Val Ile
    290                 295                 300

Asp Lys Gly Ser Ile Lys Lys Tyr Ile Pro Tyr Leu Tyr Asn Gly Leu
305                 310                 315                 320

Gln His Ser Cys Gln Asp Ile Gly Val Arg Ser Leu Val Glu Phe Arg
                325                 330                 335

Glu Lys Val Asp Ser Gly Ser Val Arg Phe Glu Phe Arg Thr Pro Ser
            340                 345                 350

Ala Gln Leu Glu Gly Gly Val His Asn Leu His Ser Tyr Glu Lys Arg
        355                 360                 365

Leu Phe Asp
    370

<210> SEQ ID NO 10
<211> LENGTH: 2697
<212> TYPE: DNA
<213> ORGANISM: Ashbya gossypii
<220> FEATURE:
<221> NAME/KEY: CDS
<222> LOCATION: 456..2033
```

<400> SEQUENCE: 10

```
atcgatttca ggagattttt ggtagcatta ttgaggtcat tagaggcgtt ctgtgacttt      60
cgacgatttg cacgcgcaga agagggcgtt caaccagcct ttcggatatt ccggttcgag     120
ttataccagc agggatcagc gcaggcacta gagtggcggg tgctaataag aggagcaggt     180
cctggaactg aagttgcaag agataagcat tgcgcggaga aggaggcggt tagagggtgc     240
aagcgagcag gatgggtct tcgatgaact tcccgtctgg gtatgtgaac aagcacacgc      300
tgcaggcaca ccgtagggc gagtgcaggg tgaaaaatat atatgcgctc gagaagcgct     360
ggggatgagt tcgtctgcaa cggcaggcgg atcttcatct gacaaaacca gctgcctaca     420
```

| | | | | |
|---|---|---|---|---|
| tcagtgcgaa gctgttcagt gatagaatag agta atg gct gct gtt gaa caa | | | | 473 |
| | Met Ala Ala Val Glu Gln | | | |
| | 1 | 5 | | |

| | | |
|---|---|---|
| gtt tct agc gtg ttt gac acc att ttg gtg ctg gac ttc ggg tcc cag | | 521 |
| Val Ser Ser Val Phe Asp Thr Ile Leu Val Leu Asp Phe Gly Ser Gln | | |
| 10 | 15 | 20 |

| | | |
|---|---|---|
| tac tcg cat ctg atc acg cgg cgg ctg cgt gag ttt aat gtg tac gcg | | 569 |
| Tyr Ser His Leu Ile Thr Arg Arg Leu Arg Glu Phe Asn Val Tyr Ala | | |
| 25 | 30 | 35 |

| | | |
|---|---|---|
| gag atg ctt ccg tgt acg cag aag atc agc gag ctg ggc tgg aag cca | | 617 |
| Glu Met Leu Pro Cys Thr Gln Lys Ile Ser Glu Leu Gly Trp Lys Pro | | |
| 40 | 45 | 50 |

| | | |
|---|---|---|
| aag ggt gtg att ttg tca ggc ggg ccg tac tcc gtg tac gcg gca gat | | 665 |
| Lys Gly Val Ile Leu Ser Gly Gly Pro Tyr Ser Val Tyr Ala Ala Asp | | |
| 55 | 60 | 65 | 70 |

| | | |
|---|---|---|
| gct ccg cac gtg gac cgg gcg gtg ttc gag ttg ggc gtt cca att ctg | | 713 |
| Ala Pro His Val Asp Arg Ala Val Phe Glu Leu Gly Val Pro Ile Leu | | |
| 75 | 80 | 85 |

| | | |
|---|---|---|
| ggc atc tgc tac ggg cta cag gag ctt gcg tgg ata gcc ggc gca gag | | 761 |
| Gly Ile Cys Tyr Gly Leu Gln Glu Leu Ala Trp Ile Ala Gly Ala Glu | | |
| 90 | 95 | 100 |

| | | |
|---|---|---|
| gtg ggg cgc ggc gag aag cgc gag tac ggg cgc gcg acg ctg cac gtg | | 809 |
| Val Gly Arg Gly Glu Lys Arg Glu Tyr Gly Arg Ala Thr Leu His Val | | |
| 105 | 110 | 115 |

| | | |
|---|---|---|
| gag gac agc gcg tgc ccg ctg ttc aac aac gtg gac agc agc acg gtg | | 857 |
| Glu Asp Ser Ala Cys Pro Leu Phe Asn Asn Val Asp Ser Ser Thr Val | | |
| 120 | 125 | 130 |

| | | |
|---|---|---|
| tgg atg tcg cac ggt gac aag ctg cac gca cta cct gcg gat ttc cac | | 905 |
| Trp Met Ser His Gly Asp Lys Leu His Ala Leu Pro Ala Asp Phe His | | |
| 135 | 140 | 145 | 150 |

| | | |
|---|---|---|
| gtc act gcg acg acg gag aac tct cct ttc tgc ggg att gca cac gac | | 953 |
| Val Thr Ala Thr Thr Glu Asn Ser Pro Phe Cys Gly Ile Ala His Asp | | |
| 155 | 160 | 165 |

| | | |
|---|---|---|
| tcg aag cca atc ttc ggg atc cag ttc cac cct gag gtg acg cac tcc | | 1001 |
| Ser Lys Pro Ile Phe Gly Ile Gln Phe His Pro Glu Val Thr His Ser | | |
| 170 | 175 | 180 |

| | | |
|---|---|---|
| tcg cag ggg aag acg ttg ctg aag aac ttt gcg gtg gag atc tgc cag | | 1049 |
| Ser Gln Gly Lys Thr Leu Leu Lys Asn Phe Ala Val Glu Ile Cys Gln | | |
| 185 | 190 | 195 |

| | | |
|---|---|---|
| gcc gcg cag acc tgg acg atg gaa aac ttc att gac acc gag atc cag | | 1097 |
| Ala Ala Gln Thr Trp Thr Met Glu Asn Phe Ile Asp Thr Glu Ile Gln | | |
| 200 | 205 | 210 |

| | | |
|---|---|---|
| cgg atc cgg acc ctt gtg ggc ccc acc gcg gaa gtc atc ggt gct gtg | | 1145 |
| Arg Ile Arg Thr Leu Val Gly Pro Thr Ala Glu Val Ile Gly Ala Val | | |
| 215 | 220 | 225 | 230 |

| | | |
|---|---|---|
| tcc ggc ggt gtc gac tcg acc gtc gct gcg aag ctg atg acc gag gcc | | 1193 |
| Ser Gly Gly Val Asp Ser Thr Val Ala Ala Lys Leu Met Thr Glu Ala | | |
| 235 | 240 | 245 |

-continued

| | | |
|---|---|---|
| atc ggc gac cgg ttc cac gcg atc ctg gtc gac aac ggt gtt ctg cgc<br>Ile Gly Asp Arg Phe His Ala Ile Leu Val Asp Asn Gly Val Leu Arg<br>250                             255                          260 | 1241 |

```
atc ggc gac cgg ttc cac gcg atc ctg gtc gac aac ggt gtt ctg cgc    1241
Ile Gly Asp Arg Phe His Ala Ile Leu Val Asp Asn Gly Val Leu Arg
            250                 255                 260 ctc aac gaa gcg gcc aat gtg aag aaa atc ctc ggc gag ggt ttg ggc    1289
Leu Asn Glu Ala Ala Asn Val Lys Lys Ile Leu Gly Glu Gly Leu Gly
                265                 270                 275 atc aac ttg act gtt gtt gac gcc tcc gaa gag ttc ttg acg aag ctc    1337
Ile Asn Leu Thr Val Val Asp Ala Ser Glu Glu Phe Leu Thr Lys Leu
        280                 285                 290 aag ggc gtc acg gac cct gag aag aag aga aag atc atc ggt aac acc    1385
Lys Gly Val Thr Asp Pro Glu Lys Lys Arg Lys Ile Ile Gly Asn Thr
295                 300                 305                 310 ttc att cat gtt ttt gag cgc gag gca gcc agg atc cag cct aag aac    1433
Phe Ile His Val Phe Glu Arg Glu Ala Ala Arg Ile Gln Pro Lys Asn
                315                 320                 325 ggc gag gag att gag ttc ctg ttg cag ggt acc cta tac cct gac gtt    1481
Gly Glu Glu Ile Glu Phe Leu Leu Gln Gly Thr Leu Tyr Pro Asp Val
        330                 335                 340 atc gag tcc att tcc ttt aag ggc cca tct cag acg atc aag acc cac    1529
Ile Glu Ser Ile Ser Phe Lys Gly Pro Ser Gln Thr Ile Lys Thr His
    345                 350                 355 cat aac gtc ggt ggt ctt ttg gac aac atg aaa ctg aag ctc att gag    1577
His Asn Val Gly Gly Leu Leu Asp Asn Met Lys Leu Lys Leu Ile Glu
360                 365                 370 cct ttg cgc gag ctt ttc aag gac gag gtg aga cac ctg gga gaa cta    1625
Pro Leu Arg Glu Leu Phe Lys Asp Glu Val Arg His Leu Gly Glu Leu
375                 380                 385                 390 ttg ggg atc tcc cac gag ttg gtc tgg aga cat ccg ttc cca ggc cca    1673
Leu Gly Ile Ser His Glu Leu Val Trp Arg His Pro Phe Pro Gly Pro
                395                 400                 405 ggt atc gcc atc cgt gtg cta ggc gag gtc acc aag gag cag gtg gag    1721
Gly Ile Ala Ile Arg Val Leu Gly Glu Val Thr Lys Glu Gln Val Glu
        410                 415                 420 att gcc aga aag gca gac cac atc tac atc gag gag atc agg aaa gca    1769
Ile Ala Arg Lys Ala Asp His Ile Tyr Ile Glu Glu Ile Arg Lys Ala
    425                 430                 435 ggt cta tac aac aag att tct caa gct ttt gct tgc ttg ctg cct gtt    1817
Gly Leu Tyr Asn Lys Ile Ser Gln Ala Phe Ala Cys Leu Leu Pro Val
440                 445                 450 aag tct gtg ggt gtc atg ggt gac cag aga acc tac gac cag gtc att    1865
Lys Ser Val Gly Val Met Gly Asp Gln Arg Thr Tyr Asp Gln Val Ile
                455                 460                 465         470 gct cta aga gca att gag acc acg gac ttc atg act gcc gac tgg tat    1913
Ala Leu Arg Ala Ile Glu Thr Thr Asp Phe Met Thr Ala Asp Trp Tyr
        475                 480                 485 cca ttt gag cac gaa ttc ttg aag cat gtc gca tcc cgt att gtt aac    1961
Pro Phe Glu His Glu Phe Leu Lys His Val Ala Ser Arg Ile Val Asn
    490                 495                 500 gag gtt gaa ggt gtt gcc aga gtc acc tac gac ata act tct aag cct    2009
Glu Val Glu Gly Val Ala Arg Val Thr Tyr Asp Ile Thr Ser Lys Pro
505                 510                 515 cca gct acc gtt gaa tgg gaa taatcaccct tgggatccgc tgactggcta       2060
Pro Ala Thr Val Glu Trp Glu
520             525 ctgtaattct atgtagtgga ttagtacgat aagttacttt tgtatgatag atgtaatcac  2120
atctggctat taaaatgact cagccgaggt aaatctaacg tcccttcaca agggtgttcc  2180
tgtgtggact tccgcctgaa tttttataga tatatagata ctctactcat gaacaacctg  2240
```

```
caaccgaata agcattagtg ccaggagaag agaaccgtgg aaatgggcca agtagaaaaa      2300
atcatattcc ttaagaataa gacagtacca gaggaccatt acgagacgat ttttgaatcg      2360
aatggcttcc agactcactt tgtacccata taacccatg aacacctgcc agatgaggtt      2420
cgcggtcgac tatccgacgc gaattacatg aaaaggttga attgtttggt ggtaacctct      2480
cagaggactg tggagtgtct ctatgaggac gttctgccct ctcttccagc tgaagcacgc      2540
aaatctcttc tcaatacgcc agtattcgtg gttgggcgtg ccactcagga atttatggag      2600
agatgcggct ttacggacgt gagaggggga tctgagactg gtaatggcgt tttgctagcg      2660
gagttaatgt aaatatgat ccagaagggc gatgggg                                2697
```

<210> SEQ ID NO 11
<211> LENGTH: 525
<212> TYPE: PRT
<213> ORGANISM: Ashbya gossypii

<400> SEQUENCE: 11

```
Met Ala Ala Val Glu Gln Val Ser Ser Val Phe Asp Thr Ile Leu Val
  1               5                  10                  15

Leu Asp Phe Gly Ser Gln Tyr Ser His Leu Ile Thr Arg Arg Leu Arg
             20                  25                  30

Glu Phe Asn Val Tyr Ala Glu Met Leu Pro Cys Thr Gln Lys Ile Ser
         35                  40                  45

Glu Leu Gly Trp Lys Pro Lys Gly Val Ile Leu Ser Gly Gly Pro Tyr
     50                  55                  60

Ser Val Tyr Ala Ala Asp Ala Pro His Val Asp Arg Ala Val Phe Glu
 65                  70                  75                  80

Leu Gly Val Pro Ile Leu Gly Ile Cys Tyr Gly Leu Gln Glu Leu Ala
                 85                  90                  95

Trp Ile Ala Gly Ala Glu Val Gly Arg Gly Glu Lys Arg Glu Tyr Gly
            100                 105                 110

Arg Ala Thr Leu His Val Glu Asp Ser Ala Cys Pro Leu Phe Asn Asn
        115                 120                 125

Val Asp Ser Ser Thr Val Trp Met Ser His Gly Asp Lys Leu His Ala
    130                 135                 140

Leu Pro Ala Asp Phe His Val Thr Ala Thr Glu Asn Ser Pro Phe
145                 150                 155                 160

Cys Gly Ile Ala His Asp Ser Lys Pro Ile Phe Gly Ile Gln Phe His
                165                 170                 175

Pro Glu Val Thr His Ser Ser Gln Gly Lys Thr Leu Leu Lys Asn Phe
            180                 185                 190

Ala Val Glu Ile Cys Gln Ala Ala Gln Thr Trp Thr Met Glu Asn Phe
        195                 200                 205

Ile Asp Thr Glu Ile Gln Arg Ile Arg Thr Leu Val Gly Pro Thr Ala
    210                 215                 220

Glu Val Ile Gly Ala Val Ser Gly Gly Val Asp Ser Thr Val Ala Ala
225                 230                 235                 240

Lys Leu Met Thr Glu Ala Ile Gly Asp Arg Phe His Ala Ile Leu Val
                245                 250                 255

Asp Asn Gly Val Leu Arg Leu Asn Glu Ala Ala Asn Val Lys Lys Ile
            260                 265                 270

Leu Gly Glu Gly Leu Gly Ile Asn Leu Thr Val Val Asp Ala Ser Glu
        275                 280                 285

Glu Phe Leu Thr Lys Leu Lys Gly Val Thr Asp Pro Glu Lys Lys Arg
```

```
          290                 295                 300
Lys Ile Ile Gly Asn Thr Phe Ile His Val Phe Glu Arg Glu Ala Ala
305                 310                 315                 320

Arg Ile Gln Pro Lys Asn Gly Glu Ile Glu Phe Leu Leu Gln Gly
                325                 330                 335

Thr Leu Tyr Pro Asp Val Ile Glu Ser Ile Ser Phe Lys Gly Pro Ser
                340                 345                 350

Gln Thr Ile Lys Thr His His Asn Val Gly Gly Leu Leu Asp Asn Met
                355                 360                 365

Lys Leu Lys Leu Ile Glu Pro Leu Arg Glu Leu Phe Lys Asp Glu Val
370                 375                 380

Arg His Leu Gly Glu Leu Leu Gly Ile Ser His Glu Leu Val Trp Arg
385                 390                 395                 400

His Pro Phe Pro Gly Pro Gly Ile Ala Ile Arg Val Leu Gly Glu Val
                405                 410                 415

Thr Lys Glu Gln Val Glu Ile Ala Arg Lys Ala Asp His Ile Tyr Ile
                420                 425                 430

Glu Glu Ile Arg Lys Ala Gly Leu Tyr Asn Lys Ile Ser Gln Ala Phe
                435                 440                 445

Ala Cys Leu Leu Pro Val Lys Ser Val Gly Val Met Gly Asp Gln Arg
450                 455                 460

Thr Tyr Asp Gln Val Ile Ala Leu Arg Ala Ile Glu Thr Thr Asp Phe
465                 470                 475                 480

Met Thr Ala Asp Trp Tyr Pro Phe Glu His Glu Phe Leu Lys His Val
                485                 490                 495

Ala Ser Arg Ile Val Asn Glu Val Glu Gly Val Ala Arg Val Thr Tyr
                500                 505                 510

Asp Ile Thr Ser Lys Pro Pro Ala Thr Val Glu Trp Glu
                515                 520                 525

<210> SEQ ID NO 12
<211> LENGTH: 1634
<212> TYPE: DNA
<213> ORGANISM: Ashbya gossypii
<220> FEATURE:
<221> NAME/KEY: CDS
<222> LOCATION: 520..1482

<400> SEQUENCE: 12
cctcgaacat ctatcttctg agctcgatag tctacgaaat cggcacacta gcctaattgc      60
cgagatgaag agctccaggg aaccgttaaa gatctgatgt tccatcttca atcaggacaa     120
atgttacggg atgtccctga cgccacagaa ggtagcctgg tggtccagac agaaaaagag     180
cctacaccaa agaagaaaca taacaagaaa aagcctccgc atcgttttgg taaatcataa     240
taggcacgat gcgcatatac cctgaccatc atagcggttc ccccgctaa ctgctccgag      300 cgggtaaccc catgtcacaa agtgactctg tctcttcgtg gtaggtgatg tcaaattttc     360
acgacttccc accccgatga gcatccgtat tcctttcat ctaaattcta atagatggct      420
tatggattct tattggcgac ttacaagcct atgtagttgg cttccctcaa gtgttcgtag     480
tctaccacct cacacccggt ctaacagctt acgagaata atg gct act aat gca      534
                                              Met Ala Thr Asn Ala
                                                1               5 atc aag ctt ctt gcg cca gat atc cac agg ggt ctg gca gag ctg gtc      582
Ile Lys Leu Leu Ala Pro Asp Ile His Arg Gly Leu Ala Glu Leu Val
         10                  15                  20
```

```
gct aaa cgc cta ggc tta cgt ctg aca gac tgc aag ctt aag cgg gat       630
Ala Lys Arg Leu Gly Leu Arg Leu Thr Asp Cys Lys Leu Lys Arg Asp
            25                  30                  35 tgt aac ggg gag gcg aca ttt tcg atc gga gaa tct gtt cga gac cag       678
Cys Asn Gly Glu Ala Thr Phe Ser Ile Gly Glu Ser Val Arg Asp Gln
        40                  45                  50 gat atc tac atc atc acg cag gtg ggg tcc ggg gac gtg aac gac cga       726
Asp Ile Tyr Ile Ile Thr Gln Val Gly Ser Gly Asp Val Asn Asp Arg
    55                  60                  65 gtg ctg gag ctg ctc atc atg atc aac gct agc aag acg gcg tct gcg       774
Val Leu Glu Leu Leu Ile Met Ile Asn Ala Ser Lys Thr Ala Ser Ala
70                  75                  80                  85 cgg cga att acg gct gtg att cca aac ttc cca tac gcg cgg cag gac       822
Arg Arg Ile Thr Ala Val Ile Pro Asn Phe Pro Tyr Ala Arg Gln Asp
                90                  95                  100 cgg aag gat aag tca cgg gcg cca att acc gcg aag ctc atg gcg gac       870
Arg Lys Asp Lys Ser Arg Ala Pro Ile Thr Ala Lys Leu Met Ala Asp
            105                 110                 115 atg ctg act acc gcg ggc tgc gat cat gtc atc acc atg gac tta cac       918
Met Leu Thr Thr Ala Gly Cys Asp His Val Ile Thr Met Asp Leu His
        120                 125                 130 gct tcg caa atc cag ggc ttc ttt gat gta cca gtt gac aac ctt tac       966
Ala Ser Gln Ile Gln Gly Phe Phe Asp Val Pro Val Asp Asn Leu Tyr
    135                 140                 145 gca gag cct agc gtg gtg aag tat atc aag gag cat att ccc cac gac      1014
Ala Glu Pro Ser Val Val Lys Tyr Ile Lys Glu His Ile Pro His Asp
150                 155                 160                 165 gat gcc atc atc atc tcg ccg gat gct ggt ggt gcc aaa cgt gcg tcg      1062
Asp Ala Ile Ile Ile Ser Pro Asp Ala Gly Gly Ala Lys Arg Ala Ser
                170                 175                 180 ctt cta tca gat cgc cta aac ttg aac ttt gcg ctg att cat aag gaa      1110
Leu Leu Ser Asp Arg Leu Asn Leu Asn Phe Ala Leu Ile His Lys Glu
            185                 190                 195 cgt gca aag gca aac gaa gtg tcc cgc atg gtt ctg gtc ggc gat gtt      1158
Arg Ala Lys Ala Asn Glu Val Ser Arg Met Val Leu Val Gly Asp Val
        200                 205                 210 acc gat aaa gtc tgc att atc gtt gac gat atg gcg gat act tgt ggt      1206
Thr Asp Lys Val Cys Ile Ile Val Asp Asp Met Ala Asp Thr Cys Gly
    215                 220                 225 acg ctg gcc aag gcg gca gaa gtg ctg cta gag cac aac gcg cgg tct      1254
Thr Leu Ala Lys Ala Ala Glu Val Leu Leu Glu His Asn Ala Arg Ser
230                 235                 240                 245 gtg ata gcc att gtt acc cac ggt atc ctt tca gga aag gcc att gag      1302
Val Ile Ala Ile Val Thr His Gly Ile Leu Ser Gly Lys Ala Ile Glu
                250                 255                 260 aac atc aac aat tcg aag ctt gat agg gtt gtg tgt acc aac acc gtg      1350
Asn Ile Asn Asn Ser Lys Leu Asp Arg Val Val Cys Thr Asn Thr Val
            265                 270                 275 cca ttc gag gag aag atg aag tta tgc ccg aag tta gat gta att gat      1398
Pro Phe Glu Glu Lys Met Lys Leu Cys Pro Lys Leu Asp Val Ile Asp
        280                 285                 290 atc tcg gca gtt ctt gcg gaa tcc att cgc cgt cta cac aat ggt gaa      1446
Ile Ser Ala Val Leu Ala Glu Ser Ile Arg Arg Leu His Asn Gly Glu
    295                 300                 305 agt atc tcc tac ctc ttt aaa aac aac cca cta tgattttgct tctcgatgct    1499
Ser Ile Ser Tyr Leu Phe Lys Asn Asn Pro Leu
310                 315                 320 ggcttcttga gggccaattt tgccgtagag gtagtatccc ttcttttat attgactatt     1559 taacgaagac tatttcttca taaatggact tcggcttcac tgtgaatctc acatgatata    1619
```

```
gttgtttcag agacc                                              1634
```

<210> SEQ ID NO 13
<211> LENGTH: 320
<212> TYPE: PRT
<213> ORGANISM: Ashbya gossypii

<400> SEQUENCE: 13

```
Met Ala Thr Asn Ala Ile Lys Leu Leu Ala Pro Asp Ile His Arg Gly
  1               5                  10                  15

Leu Ala Glu Leu Val Ala Lys Arg Leu Gly Leu Arg Leu Thr Asp Cys
             20                  25                  30

Lys Leu Lys Arg Asp Cys Asn Gly Glu Ala Thr Phe Ser Ile Gly Glu
         35                  40                  45

Ser Val Arg Asp Gln Asp Ile Tyr Ile Ile Thr Gln Val Gly Ser Gly
     50                  55                  60

Asp Val Asn Asp Arg Val Leu Glu Leu Leu Ile Met Ile Asn Ala Ser
 65                  70                  75                  80

Lys Thr Ala Ser Ala Arg Arg Ile Thr Ala Val Ile Pro Asn Phe Pro
                 85                  90                  95

Tyr Ala Arg Gln Asp Arg Lys Asp Lys Ser Arg Ala Pro Ile Thr Ala
            100                 105                 110

Lys Leu Met Ala Asp Met Leu Thr Thr Ala Gly Cys Asp His Val Ile
        115                 120                 125

Thr Met Asp Leu His Ala Ser Gln Ile Gln Gly Phe Phe Asp Val Pro
    130                 135                 140

Val Asp Asn Leu Tyr Ala Glu Pro Ser Val Val Lys Tyr Ile Lys Glu
145                 150                 155                 160

His Ile Pro His Asp Ala Ile Ile Ser Pro Asp Ala Gly Gly
                165                 170                 175

Ala Lys Arg Ala Ser Leu Leu Ser Asp Arg Leu Asn Leu Asn Phe Ala
            180                 185                 190

Leu Ile His Lys Glu Arg Ala Lys Ala Asn Glu Val Ser Arg Met Val
        195                 200                 205

Leu Val Gly Asp Val Thr Asp Lys Val Cys Ile Ile Val Asp Asp Met
    210                 215                 220

Ala Asp Thr Cys Gly Thr Leu Ala Lys Ala Ala Glu Val Leu Leu Glu
225                 230                 235                 240

His Asn Ala Arg Ser Val Ile Ala Ile Val Thr His Gly Ile Leu Ser
                245                 250                 255

Gly Lys Ala Ile Glu Asn Ile Asn Asn Ser Lys Leu Asp Arg Val Val
            260                 265                 270

Cys Thr Asn Thr Val Pro Phe Glu Glu Lys Met Lys Leu Cys Pro Lys
        275                 280                 285

Leu Asp Val Ile Asp Ile Ser Ala Val Leu Ala Glu Ser Ile Arg Arg
    290                 295                 300

Leu His Asn Gly Glu Ser Ile Ser Tyr Leu Phe Lys Asn Asn Pro Leu
305                 310                 315                 320
```

<210> SEQ ID NO 14
<211> LENGTH: 25
<212> TYPE: DNA
<213> ORGANISM: Artificial Sequence
<220> FEATURE:
<223> OTHER INFORMATION: PCR primer

```
<400> SEQUENCE: 14
gatgctagag accgcggggt gcaac                                    25

<210> SEQ ID NO 15
<211> LENGTH: 26
<212> TYPE: DNA
<213> ORGANISM: Artificial Sequence
<220> FEATURE:
<223> OTHER INFORMATION: PCR primer

<400> SEQUENCE: 15
tgtccgccat gtcgtctaca ataata                                   26

<210> SEQ ID NO 16
<211> LENGTH: 25
<212> TYPE: DNA
<213> ORGANISM: Artificial Sequence
<220> FEATURE:
<223> OTHER INFORMATION: PCR primer

<400> SEQUENCE: 16
atatcttgat gaagacgttc accgt                                    25

<210> SEQ ID NO 17
<211> LENGTH: 25
<212> TYPE: DNA
<213> ORGANISM: Artificial Sequence
<220> FEATURE:
<223> OTHER INFORMATION: PCR primer

<400> SEQUENCE: 17
gataatgacg gcttggccgg gaaga                                    25

<210> SEQ ID NO 18
<211> LENGTH: 25
<212> TYPE: DNA
<213> ORGANISM: Artificial Sequence
<220> FEATURE:
<223> OTHER INFORMATION: PCR primer

<400> SEQUENCE: 18
ggcatcaacc tcgaggaggc gaacc                                    25

<210> SEQ ID NO 19
<211> LENGTH: 25
<212> TYPE: DNA
<213> ORGANISM: Artificial Sequence
<220> FEATURE:
<223> OTHER INFORMATION: PCR primer

<400> SEQUENCE: 19
cagaccggcc tcgaccagca tcgcc                                    25

<210> SEQ ID NO 20
<211> LENGTH: 25
<212> TYPE: DNA
<213> ORGANISM: Artificial Sequence
<220> FEATURE:
<223> OTHER INFORMATION: PCR primer

<400> SEQUENCE: 20
tggaccgggc ggtgttcgag ttggg                                    25

<210> SEQ ID NO 21
<211> LENGTH: 25
```

-continued

```
<212> TYPE: DNA
<213> ORGANISM: Artificial Sequence
<220> FEATURE:
<223> OTHER INFORMATION: PCR primer

<400> SEQUENCE: 21
aggctggatc ctggctgcct cgcgc                                    25
```